(12) United States Patent
Braxmeier et al.

(10) Patent No.: US 7,629,385 B2
(45) Date of Patent: Dec. 8, 2009

(54) SPHINGOLIPID-DERIVED PHARMACEUTICAL COMPOSITIONS

(75) Inventors: Tobias Braxmeier, Dresden (DE); Tim Friedrichson, Dresden (DE); Wolfgang Fröhner, Walldorf (DE); Gary Jennings, Dresden (DE); Georg Schlechtingen, Dresden (DE); Cornelia Schroeder, Berlin (DE); Hans-Joachim Knölker, Dresden (DE); Kai Simons, Dresden (DE); Marino Zerial, Dresden (DE); Teymuras Kurzchalia, Dresden (DE)

(73) Assignees: Max-Planck-Gesellschaft zur Förderung der Wissenschaften E.V., Munich (DE); Technische Universität Dresden, Dresden (DE); Jado Technologies GmbH, Dresden (DE)

( * ) Notice: Subject to any disclaimer, the term of this patent is extended or adjusted under 35 U.S.C. 154(b) by 12 days.

(21) Appl. No.: 11/571,354

(22) PCT Filed: Jun. 29, 2005

(86) PCT No.: PCT/EP2005/007033
§ 371 (c)(1),
(2), (4) Date: Aug. 8, 2007

(87) PCT Pub. No.: WO2006/002909
PCT Pub. Date: Jan. 12, 2006

(65) Prior Publication Data
US 2008/0090913 A1    Apr. 17, 2008

Related U.S. Application Data

(60) Provisional application No. 60/636,471, filed on Dec. 16, 2004.

(30) Foreign Application Priority Data
Jun. 29, 2004  (EP) .................................. 04015248

(51) Int. Cl.
*A61K 31/13* (2006.01)
*A61K 31/16* (2006.01)

(52) U.S. Cl. ...................................... 514/579; 514/183
(58) Field of Classification Search ........................ None
See application file for complete search history.

(56) References Cited

FOREIGN PATENT DOCUMENTS

| | | |
|---|---|---|
| DE | 19841794 | 3/2000 |
| EP | 1 291 430 | 3/2003 |
| JP | 08 113535 | 5/1996 |
| WO | WO 94/10991 | 10/1993 |
| WO | WO 98/02153 | 1/1998 |
| WO | WO 99/41266 | 8/1999 |
| WO | WO 00/59517 | 10/2000 |
| WO | WO 01/22957 | 4/2001 |
| WO | WO 2004/006483 | 5/2004 |

OTHER PUBLICATIONS

Rosenwald et. al., The Journal of Biological Chemistry (1993) 268:4577-4579.*
McReynolds et. al., Bioorganic and Medicinal Chemistry (2002) 10:625-637.*
"Inhibitor against nerve cell degeneration or death—comprises N-acyl-sphingosine or sphingo-myelinase, used for treating degenerative diseases or injuries e.g. trauma and Alzheimer's disease," Database WPI, Derwent Publications Ltd., AN 1996/272724, 1996.
Anderson et al., "Bound simian virus 40 translocates to caveolin-enriched membrane domains, and its entry is inhibited by drugs that selectively disrupt caveolae," *Molecular Biology of the Cell*, 7: 1825-1834, 1996.
Damm et al., "Clathrin- and caveolin-1-independent endocytosis: entry of simian virus 40 into cells devoid of caveolae," *The Journal of Cellular Biology*, 168: 477-488, 2005.
Gidwani et al., "Disruption of lipid order by short-chain ceramides correlates with inhibition of phospholipase D and downstream signaling by FceRI," *Journal of Cell Science*, 116: 3177-3187, 2003.
Hussey et al., "Synthesis of chimeric 7alpha-substituted estradiol derivatives linked to cholesterol and cholesterylamine," *Org. Lett.*, 4: 415-418, 2002.
Ito, "N-acylsphingosine and sphingomyelinase as inhibitors of neuron degeneration and death," Chemicals Abstracts Service, Database accession No. 1996:464360, 1996.
Koskinen and Koskinen, "Sphingosine, an enigmatic lipid: a review of recent litature synthesis," *Synthesis*, 1075-1091, 1998.
Koskinen and Koskinen, "Total synthesis of sphingosine and its analogs," *Methods of Enzymologys*, 311:458-479, 1998.
Nguyen et al., "Practical synthetic route to functionalized rhodamine dyes," *Org. Lett.*, 5: 3245-3248, 2003.
Pelkmans et al., "Local Actin Polymerication and Dynamin Recruitment in SV40-Inuduced Internalization of Caveolae," *Science*, 296: 535-539, 2002.
Pelkmans et al., "Caveolar endocytosis of simina virus 40 reveals a new two-step vesicular-transport pathway to the ER," *Nature Cell Biol.*, 3: 473-483, 2001.
Rosenwald and Pagano, "Inhibition of Glycoprotein Traffic through the Secretory Pathway by Ceramide," *The Journal of Biological Chemistry*, 268: 4577-4579, 1993.
Sieczkarski and Whittaker, "Differential Requirements of Rab5 and Rab7 for Endocytosis of Influenza and Oether Enveloped Viruses," *Traffic*, 4: 333-343.
Simons and Vaz, "Model Systems, lipid rafts, and cell membrances," *Annu. Rev. Biophys. Biomol. Struct.*, 33: 269-295, 2004.
Stang et al., "Major histocompatibility complex class I molecules mediate association of SV40 with caveolae," *Mol. Biol. Cell*, 8: 47-57, 1997.

(Continued)

Primary Examiner—Frederick Krass
Assistant Examiner—Marcos Sznaidman
(74) Attorney, Agent, or Firm—Fulbright & Jaworski L.L.P.

(57) ABSTRACT

The present invention relates to specific sphingolipids/sphingolipid derivatives as pharmaceutical compositions as well as their use in the preparation of medicaments for the treatment, prevention and/or amelioration of disorders relating to pathological processes in lipid rafts.

9 Claims, No Drawings

OTHER PUBLICATIONS

Wang et al., "Fluorescence-based evaluation of the partitioning of lipids and lipidated peptides into liquid-ordered lipid microdomains: a model for molecular partitioning into 'lipid rafts'," *Biophys. J.*, 79: 919-933, 2000.

Wang et al., "Relationship between sterol/steroid structure and participation in ordered lipid domains (lipid rafts): implications for lipid raft structure and function," *Biochemistry*, 43: 1010-1018, 2004.

European Search Report, mailed Oct. 17, 2007.

Rosenwald and Pagano, "Inhibition of glycoprotein traffic through the scretory pathway by ceramide," *J. Bio. Chem.*, 268:4577-4579, 1993.

European Search Report issued in European Application No. 08021735.9, mailed Aug. 6, 2009.

* cited by examiner

SPHINGOLIPID-DERIVED PHARMACEUTICAL COMPOSITIONS

The present invention relates to specific sphingolipids/sphingolipid derivatives as pharmaceutical compositions as well as their use in the preparation of medicaments for the treatment, prevention and/or amelioration of disorders relating to pathological processes in lipid rafts.

The lipid bilayer that forms cell membranes is a two dimensional liquid the organization of which has been the object of intensive investigations for decades by biochemists and biophysicists. Although the bulk of the bilayer has been considered to be a homogeneous fluid, there have been repeated attempts to introduce lateral heterogeneities, lipid microdomains, into our model for the structure and dynamics of the bilayer liquid (Glaser, Curr. Opin. Struct. Biol. 3 (1993), 475-481; Jacobson, Comments Mol. Cell. Biophys. 8 (1992), 1-144; Jain, Adv. Lipid Res. 15 (1977), 1-60; Winchil, Curr. Opin. Struct. Biol. 3 (1993), 482-488.

The realization that epithelial cells polarize their cell surfaces into apical and basolateral domains with different protein and lipid compositions in each of these domains, initiated a new development that led to the "lipid raft" concept (Simons, Biochemistry 27 (1988), 6197-6202; Simons, Nature 387 (1997), 569-572). The concept of assemblies of sphingolipids and cholesterol functioning as platforms for membrane proteins was promoted by the observation that these assemblies survived detergent extraction, and are referred to as detergent resistant membranes, DRM (Brown, Cell 68 (1992), 533-544). This was an operational break-through where raft-association was equated with resistance to Triton-X100 extraction at 4° C. The addition of a second criterion, depletion of cholesterol using methyl-β-cyclodextrin (Ilangumaran, Biochem. J. 335 (1998), 433-440; Scheiffele, EMBO J. 16 (1997), 5501-5508), leading to loss of detergent resistance, prompted several groups in the field to explore the role of lipid microdomains in a wide spectrum of biological reactions. There is now increasing support for a role of lipid assemblies in regulating numerous cellular processes including cell polarity, protein trafficking and signal transduction.

Cell membranes are two-dimensional liquids. Thus, lateral heterogeneity implies liquid-liquid immiscibility in the membrane plane. It has been well known that hydrated lipid bilayers undergo phase transitions as a function of temperature. These transitions, which occur at defined temperatures for each lipid species, always involve some change in the order of the system. The most important of these transitions is the so-called "main" or "chain-melting" transition in which the bilayer is transformed from a highly ordered quasi-two dimensional crystalline solid to a quasi-two dimensional liquid. It involves a drastic change in the order of the systems, in particular of the translational (positional) order in the bilayer plane and of the conformational order of the lipid chains in a direction perpendicular to this plane. Translational order is related to the lateral diffusion coefficient in the plane of the membrane and conformational order is related to the trans/gauche ratio in the acyl chains. The main transition has been described as an ordered-to-disordered phase transition, so that the two phases may be labeled as solid-ordered ($s_o$) below the transition temperature and liquid-disordered ($l_d$) above that temperature. Cholesterol and phospholipids are capable of forming a liquid-ordered ($l_o$)) phase that can coexist with a cholesterol-poor liquid-disordered ($l_d$) phase thereby permitting phase coexistence in wholly liquid phase membranes (Ipsen, Biochem. Biophys. Acta 905 (1987) 162-172; Ipsen, Biophys. J. 56 (1989), 661-667). Sterols do so as a result of their flat and rigid molecular structure, which is able to impose a conformational ordering upon a neighboring aliphatic chain (Sankaram, Biochemistry 29 (1990), 10676-10684), when the sterol is the nearest neighbor of the chain, without imposing a corresponding drastic reduction of the translational mobility of the lipid (Nielsen, Phys. Rev. E. Stat. Phys. Plasmas Fluids Relat. Interdiscip. Topics 59 (1999), 5790-5803). Due to the fact that the sterol does not fit exactly in the crystalline lattice of an $s_o$ (gel) lipid bilayer phase it will, if it dissolves within this phase, disrupt the crystalline translational order without, however, significantly perturbing the conformational order. Thus, cholesterol at adequate molar fractions can convert $l_d$ or $s_o$ lipid bilayer phases to liquid-ordered ($l_o$) phases.

Lipid rafts are lipid platforms of a special chemical composition (rich in sphingomyelin and cholesterol in the outer leaflet of the cell membrane) that function to segregate membrane components within the cell membrane. Rafts are understood to be relatively small (30-50 nm in diameter, estimates of size varying considerably depending on the probes used and cell types analysed) but they can be coalesced under certain conditions. Their specificity with regard to lipid composition is reminiscent of phase separation behavior in heterogeneous model membrane systems. In fact, many of their properties with regard to chemical composition and detergent solubility are similar to what is observed in model systems composed of ternary mixtures of an unsaturated phosphatidylcholine, sphingomyelin (or a long-chain saturated phosphatidylcholine), and cholesterol (de Almeida, Biophys. J. 85 (2003), 2406-2416). Rafts may be considered domains of a $l_o$ phase in a heterogeneous l phase lipid bilayer composing the plasma membrane. What the other coexisting phase (or phases) is (or are) is not clear at present. There is consensus that the biological membrane is a liquid, so $s_o$ phase coexistence may be ignored for most cases. Whether the other phase (phases) is (are) $l_d$ or $l_o$ phases will depend upon the chemical identity of the phospholipids that constitute this phase (these phases) and the molar fraction of cholesterol in them. Rafts may be equated with a liquid-ordered phase and refer to the rest of the membrane as the non-raft liquid phase. Within the framework of thermodynamics, a phase is always a macroscopic system consisting of large number of molecules. However, in lipid bilayers the phases often tend to be fragmented into small domains (often only a few thousand molecules) each of which, per se, may not have a sufficient number of molecules to strictly satisfy the thermodynamic definition of a phase. The liquid-ordered raft phase thus comprises all the domains (small or clustered) of the raft phase in the membranes. The rest of the membrane surrounding the rafts, the liquid phase, may be a homogeneous percolating liquid phase or may be further subdivided into liquid domains not yet characterized. Pralle, J. Cell. Biol. (2000) 148, 997-1008 employed photonic force microscopy to measure the size of lipid rafts and found that rafts in the plasma membrane of fibroblasts diffuse as assemblies of 50 nm diameter, corresponding to a surface area covered by about 3,000 sphingolipids. Based on data from cultured baby hamster kidney (BHK) cells, whose lipid composition and organelle surface area have been examined in detail, it appears that an individual cell has a surface area of approximately 2,000 $\mu m^2$. The lipid composition of the cell plasma membrane contains 26% phosphatidylcholine, 24% sphingomyelin, and 12% glycosphingolipids. Due to the asymmetric nature of the lipid organization in the plasma membrane, most of the sphingolipids occupy the outer leaflet of the bilayer, while less than half of the phosphatidylcholine has been estimated to be in this leaflet.

Assuming that most of the sphingolipid is raft-associated, rafts would cover more than half of the cell surface. The density of membrane proteins has been estimated to be around 20,000 molecules per $\mu m^2$. Thus, the plasma membrane would accordingly contain about $40\times10^6$ protein molecules. The number of 50-nm rafts would be about $10^6$, and if the density of proteins is the same in rafts as in the surrounding bilayer, each raft would carry about 20 protein molecules. If BHK cells are representative, it follows that the density of rafts floating in the fibroblast plasma membrane is high. If $20\times10^6$ raft protein molecules were distributed more or less randomly, each raft would likely contain a different subset of proteins. A kinase attached to the cytosolic leaflet of a raft is, therefore, unlikely to meet its substrate in the same individual raft. The small size of an individual raft may be important for keeping raft-borne signaling proteins in the "off" state. Accordingly, for activation to occur, many rafts have to cluster together, forming a larger platform, where the protein participants in a signal transduction process can meet, undisturbed by what happens outside the platform. Thus, rafts are small, and, when activated, they cluster to form larger platforms in which functionally related proteins can interact. One way to analyze raft association and clustering is to patch raft and nonraft components on the surface of living cells by specific antibodies (Harder, J Cell Biol. 141 (1998), 929-942; Janes, Semin. Immunol. 12 (2000), 23-34). If two raft components are cross-linked by antibodies, they will form overlapping patches in the plasma membrane. However, patching of a raft protein and a nonraft marker such as the transferrin receptor leads to the formation of segregated patches. Co-patching of two raft components is dependent on the simultaneous addition of both antibodies to the cells. If antibodies are added sequentially, segregated patches predominate. Notably, the patching behavior is cholesterol-dependent. As a consequence of the small size and the heterogeneous composition of individual rafts, these structures must be clustered in specific ways if signaling is to ensue. One example of such a raft clustering process encountered in daily clinical practice is the IgE signaling during the allergic immune response (Sheets, Curr. Opin. Chem. Biol. 3 (1999), 95-99; Holowka, Semin. Immunol. 13 (2001), 99-105). The allergen that elicits the allergic reaction by stimulating the degranulation of a mast or basophilic cell is multivalent, binding several IgE antibody molecules. Cross-linking of two or more IgE receptors [Fc($\epsilon$)RI ] increases their association with rafts, as measured by increased detergent resistance. Within the rafts, cross-linked Fc($\epsilon$)RI becomes tyrosine phosphorylated by raft-associated Lyn, a double-acylated Src-related kinase. The Fc($\epsilon$)RI phosphorylation recruits Syk-related kinases, which are activated and lead to binding and scaffolding of downstream signaling molecules and, finally, to the formation of a signaling platform. This structure includes the raft protein LAT (linker of activation of T cells), which guides the clustering of additional rafts into the expanding platform (Rivera, Int. Arch. Allergy Immunol. 124 (2001), 137-141). Signaling leads to calcium mobilization, which triggers the release of preformed mediators such as histamine from the intracellular stores. The more participants are collected into the raft platform, the higher the signaling response. Uncontrolled amplification of the signaling cascade by raft clustering might trigger hyperactivation, with life-threatening consequences such as Quinke edema and allergic shock. The whole signaling assembly can be dissociated by dephosphorylation or downregulated by internalization of the components by endocytosis (Xu, J. Cell Sci. 111 (1998), 2385-2396). Thus, in IgE signaling, lipid rafts serve to increase the efficiency by concentrating the participating proteins into fluid microdomains and limiting their lateral diffusion so that proteins remain at the site of signaling. Even a small change of partitioning into lipid rafts can, through amplification, initiate a signaling cascade or prompt a deleterious overshoot, as occurs in allergic reactions (Kholodenko, Trends Cell Biol. 10 (2000), 173-178). Another clinically relevant example of raft clustering is the pathogenic mechanisms of pore-forming toxins, which are secreted by *Clostridium, Streptococcus*, and *Aeromonas* species, among other bacteria. These toxins may cause diseases ranging from mild cellulites to gaseous gangrene and pseudomembranous colitis. Best studied is the toxin aerolysin from the marine bacterium *Aeromonas hydrophila*. Aerolysin is secreted and binds to a GPI-anchored raft protein on the surface of the host cell. The toxin is incorporated into the membrane after proteolysis and then heptamerizes in a raft-dependent manner to form a raft-associated channel through which small molecules and ions flow to trigger the pathogenic changes. The oligomerization of aerolysin can be triggered in solution but occurs at more than $10^5$-fold lower toxin concentration at the surface of the living cell. This enormous increase in efficiency is due to activation by raft binding and by concentration into raft clusters, which is driven by the oligomerization of the toxin. Again, a small change can lead to a huge effect by amplification of raft clustering (Lesieur, Mol. Membr. Biol. 14 (1997), 45-64; Abrami, J. Cell Biol. 147 (1999), 175-184).

Lipid rafts contain specific sets of proteins (van Meer, Annu. Rev. Cell Biol. 5 (1989), 247-275; Simons, Annu. Rev. Biophys. Biomol. Struct. 33 (2004), 269-295). These include, inter alia, GPI-anchored proteins, doubly acylated proteins such as tyrosine kinases of the src family, G$\alpha$ subunits of heteromeric G proteins and endothelial nitric oxide synthase, the cholesterol- and palmitate-linked hedgehog protein and other palmitate-linked proteins, as well as transmembrane proteins. Proteins with attached saturated acyl chains and cholesterol can be associated with liquid-ordered raft domains. Studies with model membranes have confirmed that peptides containing such lipid modifications associate with liquid-ordered domains (Wang, Biophys. J. 79 (2000) 919-933). It should be noted that the GPI anchors differ in their fatty acid composition. Some GPI anchors contain unsaturated acyl chains, and how these interact with lipid rafts remains to be studied.

Transmembrane proteins, since they cross the bilayer, may disrupt the packing of the liquid-ordered domain. Yet, the lo phase is a liquid phase and therefore does not have long-range order in the membrane plane. Association of proteins with lipid rafts can be viewed as a simple solubility problem described by an equilibrium partition coefficient for partitioning of the protein between two coexisting phases, or it can be understood to require some chemical affinity for raft lipids. Several proteins interact with cholesterol. Caveolin is the prime example (Murata, Proc. Natl. Acad. Sci. USA 92 (1995), 10339-10343). There are also examples of receptor proteins interacting with glycosphingolipids including gangliosides (Hakomori, Proc. Natl. Acad. Sci. USA 99 (2002), 225-232). A structural protein motif has been identified for binding to sphingolipids (Mahfoud, J. Biol. Chem. 277 (2002), 11292-11296). Recent results also demonstrate that proteins can exist in different states depending on the membrane environment. Glutamate receptors, which are G protein-coupled heptahelical transmembrane proteins, are in a low-affinity state when reconstituted into membranes lacking cholesterol. The receptor changes its conformation in liquid-ordered cholesterol-containing membranes and now binds its ligand with high affinity (Eroglu, Proc. Natl. Acad. Sci. USA. 100 (2003), 10219-10124). The EGF receptor is activated by interaction with the ganglioside GM3 and inactivated by cholesterol depletion (Miljan, Sci. STKE. 160 (2002), 15). The receptor seems to depend on the lipid environment for high-affinity binding capability. One way to view this differential behavior would be to consider the protein as a solute in the bilayer solvent of the membrane. If the lipid bilayer has two phases, each phase is a different solvent. The protein has a conformation that depends on its environment and therefore depends on the bilayer solvent phase in which it is dissolved. So one can expect that in a nonraft domain it will have one conformation, and in the raft domain it will have another. The receptor activation would depend on the partition coefficient between the different lipid domains in the bilayers and upon phase coexistence. Another issue is the length of the transmembrane domains of the protein, because a liquid-ordered bilayer is thicker than a liquid-disordered one. These parameters play a role in protein sorting to the cell surface (Bretscher, Science 261 (1993), 1280-1281). But how precisely the transmembrane domains should be matched with the thickness of the bilayer is an open issue. So far, no detailed analysis has been carried out of how different transmembrane proteins having different transmembrane domain lengths partition into liquid-ordered and liquid-disordered domains. The transmembrane domains of single-span transmembrane proteins in the plasma membrane are usually longer than the transmembrane domains of proteins that reside in the Golgi complex or in the endoplasmic reticulum.

Anderson, Mol. Biol. Cell 7 (1996), 1825-1834 demonstrates that treatment of CV-1 or HeLa cells with the phorbol ester PMA or the macrolide polyene antibiotics Nystatin and Filipin blocked infection by Simian Virus 40 (SV40) in a reversible manner. Phorbol esters, well-known tumor promoters, are activators of protein kinase C and disrupt caveolae by blocking their invaginations (Smart (1994) J. Cell Biol. 124, 307-313). The cholesterol-binding drugs nystatin and filipin represent members of the polyene antimycotica, such as the structurally similar amphotericin B, and are widely used in standard therapy for the treatment of fungal infections. Anderson and colleagues speculate that the selective disruption of caveolae due to cholesterol depletion by those drugs is causal for the observed effect and that caveolae might mediate virus entry.

Gidwani, J. Cell Sci. 116 (2003), 3177-3187 describes an in vitro assay employing specific amphiphiles to disrupt lipid rafts. It is speculated that certain ceramides may serve as useful probes for investigating the role of plasma membrane structure and of phospholipase D activity in cellular signaling.

Wang, Biochemistry 43 (2004), 1010-1018 investigates the relationship between sterol/steroid structures and participation in lipid rafts. These authors consider this question of interest, since sterols may be used to distinguish biological processes dependent on cholesterol in cells from those processes that can be supported by any raft environment. Interestingly, Wang and colleagues have found steroids which promoted the formation of ordered domains in biological membranes.

WO 01/22957 teaches the use of gangliosides for the modulation of sphingolipid/cholesterol microdomains and it is taught that gangliosides provoke a modulation of rafts by displacement/replacement of proteins, in particular GPI-APs. It is speculated that gangliosides, ganglioside derivatives or cholesterol derivatives may be used in a clinical setting to modulate the sphingolipid-cholesterol microdomain in particular by influencing the location of anchor proteins, acetylated proteins, kinases and/or cholesterol anchor proteins.

A problem underlying the present invention is the provision of means and methods for clinical and/or pharmaceutical intervention in disorders linked to and/or associated with biological/biochemical processes regulated by lipid rafts.

The solution to this technical problem is achieved by providing the embodiments characterized herein below as well as in the claims.

Accordingly, the present invention provides a pharmaceutical composition comprising a compound having the following formula 1:

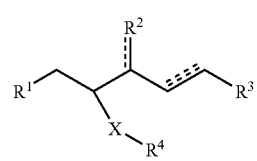

or a pharmaceutically acceptable salt, derivative, solvate or prodrug thereof.

Also are provided compounds of formula 1 for use in the preparation of a pharmaceutical composition for the treatment, prevention and/or amelioration of a disease/disorder caused by a biochemical/biophysical pathological process occurring on, in or within lipid rafts.

In the formulae provided herein, === is used to represent a single bond or a double bond, and ≡≡≡ is employed to denote a single bond, a double bond or a triple bond.

"Hydrocarbon" is used to denote a straight chain or branched, saturated or unsaturated, non-cyclic or cyclic, but non-aromatic, group based on carbon and hydrogen atoms. The hydrocarbon group can also contain combinations of these groups. For example, a hydrocarbon group can, among others, include an alkyl group, an alkenyl group, an alkynyl group, a cycloalkyl group, a cycloalkenyl group, an alkylene-cycloalkyl group, a cycloalkylene-alkyl group, an alkylene-cycloalkenyl group and a cycloalkenylene-alkyl group. Cycloalkyl and cycloalkylene groups preferably have 3 to 8 carbon atoms in their ring. Cycloalkenyl and cycloalkenylene groups preferably have 5 to 8 carbon atoms in their ring.

Furthermore, the general formulae given in the present invention are intended to cover all possible stereoisomers and diastereomers of the indicated compounds. Preferably, the stereochemical configurations in the claimed compounds are as in naturally occurring sphingosine.

X is directionally selected from NH, NHCO, NHCONH, $NHCO_2$ and $NHSO_2$, preferably NH, NHCO or NHCONH, more preferably NHCO.

$R^1$ is OR, $NR_2$ or $OPO_3^{2-}$, wherein R is H or $C_{1-4}$ alkyl. Preferably, $R^1$ is OH or $OPO_3^{2-}$, more preferably OH. $R^1$ is also envisaged to be $OCO(C_{1-4}$ alkyl).

$R^2$ is $NH_2$, $NH(C_{1-4}$ alkyl), OH, H, halogen or O, provided that if $R^2$ is O then === is a double bond, in all other cases === is a single bond. $R^2$ is also envisaged to be $N(C_{1-4}$ alkyl)$_2$ or $O(C_{1-4}$ alkyl). Preferably, $R^2$ is OH of $OCH_3$.

$R^3$ is a $C_{9-25}$, preferably $C_{9-19}$, hydrocarbon group, wherein one or more hydrogens are optionally replaced by halogen. Preferably, $R^3$ is a $C_{9-19}$ hydrocarbon group including one or more trans double bonds or a $C_{9-19}$ alkyl group. More preferably, $R^3$ is a $C_{13-15}$ alkyl group $R^4$ is a $C_{1-5}$ hydrocarbon group, wherein one or more hydrogens are optionally replaced by halogen; a $C_{3-8}$ cycloalkyl ring optionally substituted by one or more $C_{1-4}$ alkyl groups or halogens; a $(C_{3-8}$ cycloalkyl)methylene group, wherein the cycloalkyl ring is optionally substituted by one or more $C_{1-4}$ alkyl groups or halogens; a [2-($C_{3-8}$ cycloalkyl)]ethylene group, wherein the cycloalkyl ring is optionally substituted by one or more $C_{1-4}$ alkyl groups or halogens; a 1-adamantyl group, a (1-adamantyl)methylene group, a (1-adamantyl)ethylene group; or a $C_{6-30}$, preferably $C_{6-24}$, hydrocarbon group including one or more cis double bonds, wherein one or more hydrogens are optionally replaced by halogen. A $C_{6-30}$, preferably $C_{6-24}$, hydrocarbon group optionally including one or more trans double bonds, wherein one or more hydrogens are optionally replaced by halogen, is also envisaged as substituent $R^4$. Furthermore, it is envisaged that one of the hydrogen atoms on the terminal carbon atom in the $C_{6-30}$ and the $C_{6-24}$ hydrocarbon groups can be optionally be replaced by OH, O($C_{1-4}$ alkyl), OCO ($C_{1-4}$ alkyl).

$R^4$ can also be a group of the following formula 2:

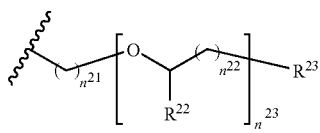

2

$n^{21}$ is an integer from 1 to 3, with the proviso that $n^{21}$ is not 1 if X is NH, NHCONH or NHCO$_2$.

$n^{22}$ is an integer of 1 or 2, preferably 1.

$n^{23}$ is an integer from 0 to 5, preferably 1 to 4.

Each $R^{22}$ is independently H or $C_{1-3}$ alkyl, preferably H or CH$_3$.

$R^{23}$ is O—$R^{21}$. $R^{23}$ is also envisaged to be NH—$R^{24}$.

$R^{21}$ is $C_{1-4}$ alkyl. $R^{21}$ is also envisaged to be CO($C_{1-4}$alkyl) or H. Preferably, $R^{21}$ is CH$_3$ or COCH$_3$.

$R^{24}$ is $C_{1-4}$ alkyl, CO($C_{1-4}$alkyl) or H. Preferably, $R^{24}$ is COCH$_3$ or H.

$R^4$ can also be H, provided that X is NH or NHCONH.

Preferably, $R^4$ is $C_{1-5}$ alkyl, $C_{5-7}$ cycloalkyl optionally substituted by one or more $C_{1-4}$ alkyl groups; 1-adamantyl; or $C_{6-20}$ alkenyl optionally containing one or more trans double bonds. In another alternative even more preferred embodiment, $R^4$ is the group of formula 2. In cases where X is NH or NHCONH, $R^4$ is H in another alternative preferred embodiment.

In accordance with the present invention it was surprisingly found that biological and/or biochemical processes involved in human diseases and disorders may be influenced by disrupting lipid rafts. This interferes with the partitioning of regulatory molecules within lipid rafts, the formation of protein complexes with lipid rafts and/or the clustering of lipid rafts, thus preventing a diseased status. Accordingly, provided herein are specific molecules, namely sphingolipid derivatives, which are capable of interfering with biological processes, in particular pathological processes taking place in, on, or within lipid rafts of cells, preferably diseased cells. These molecules are considered "disrafters" in accordance with this invention. Disrafters are either capable of inhibiting biosynthesis of raft components, of inhibiting or modulating the incorporation (transport) of raft components into membranes, of extracting major components of rafts from the membrane or of inhibiting interactions between raft component(s) by intercalating between them. It is also envisaged that "disrafters" are compounds which are capable of altering the size of lipid rafts and, thereby, inhibit (a) biological function(s) in said rafts. Accordingly, also an "augmentation" of lipid raft volume or size is considered as a disrafting process induced by the compounds provided herein. In particular, the compounds provided herein are useful in the biological process described herein above, inter alia, the prevention/inhibition of interactions between raft components by intercalation into the lipid rafts.

As documented in the appended examples the disrafting property of the compounds provided herein is determined and verified by distinct biochemical, biophysical and/or cell culture experiments. These assays comprise a disrafting liposome raftophile assay (D-LRA), a virus budding assay, a virus reproduction and infectivity assay, a degranulation assay, a SV40 infectivity assay as well as an HIV infectivity assay. The technical details are given in the appended examples.

The compounds provided herein are particularly useful in the treatment (as well as prevention and/or amelioration) of human diseases or disorders. Compounds provided herein have been scrutinized in specific biophysical/biochemical tests and have been further evaluated in cell-based disease/disorder models.

Accordingly, the compounds described herein are also useful in the treatment, prevention and/or amelioration of a disease/disorder caused by (a) biochemical/biophysical pathological process(es) occurring on, in or within lipid rafts. Corresponding examples of such diseases/disorders as well as of such biochemical/biophysical processes are given herein. The term biochemical/biophysical pathological process occurring on, in or within lipid rafts, accordingly, means for example, pathogen-induced abnormal raft clustering upon viral or bacterial infections, the formation of oligomeric structures of (bacterial) toxins in lipid rafts upon infection with pathogens, or the enhanced activity of signaling molecules (like immunoglobulin E receptor) in lipid rafts. Also a tighter than normal packing of lipid rafts/lipid raft components is considered a "biochemical/biophysical pathological process" in accordance with this invention.

The following compounds 10a to 10h are preferred examples of compound 1.

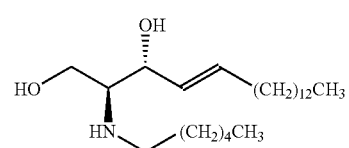

10a

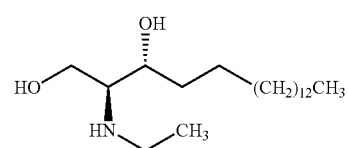

10b

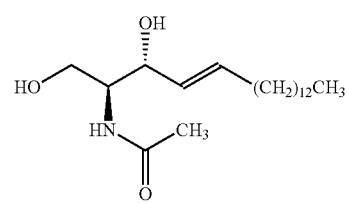

10c

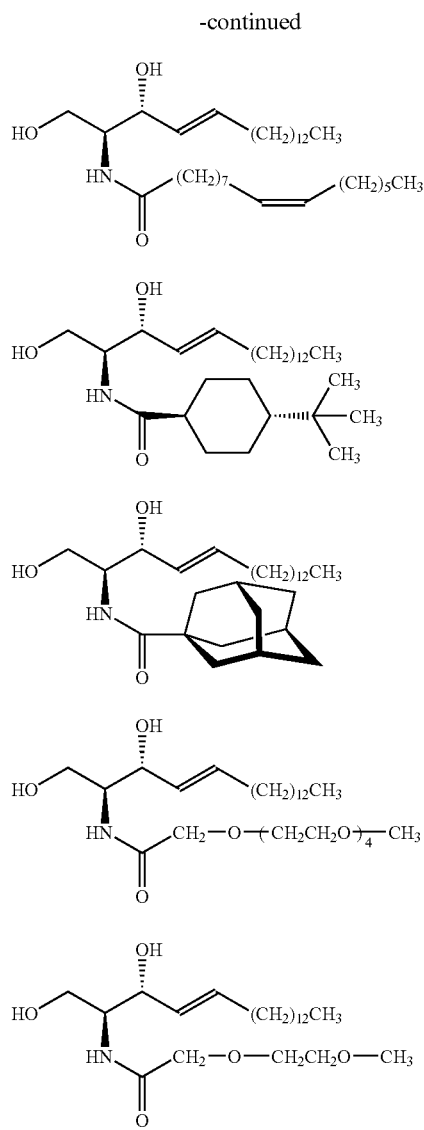
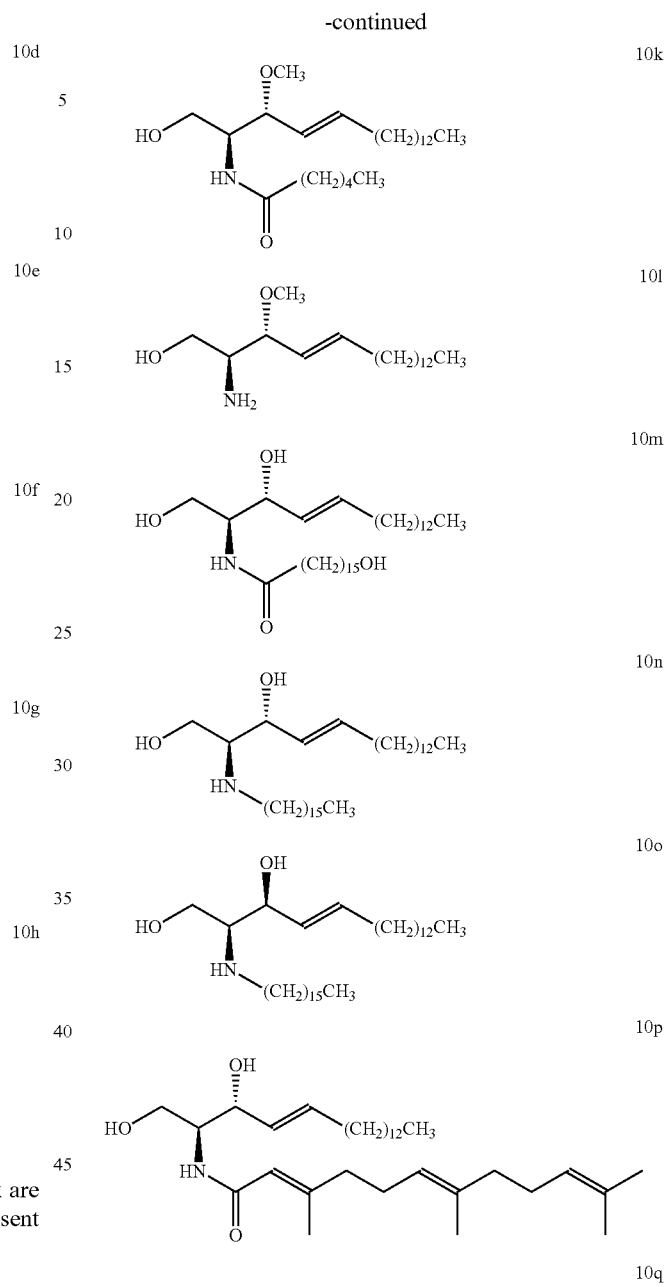
The following compounds 10i to 10s and 10u to 10x are also preferred as compounds of formula 1 in the present pharmaceutical composition:
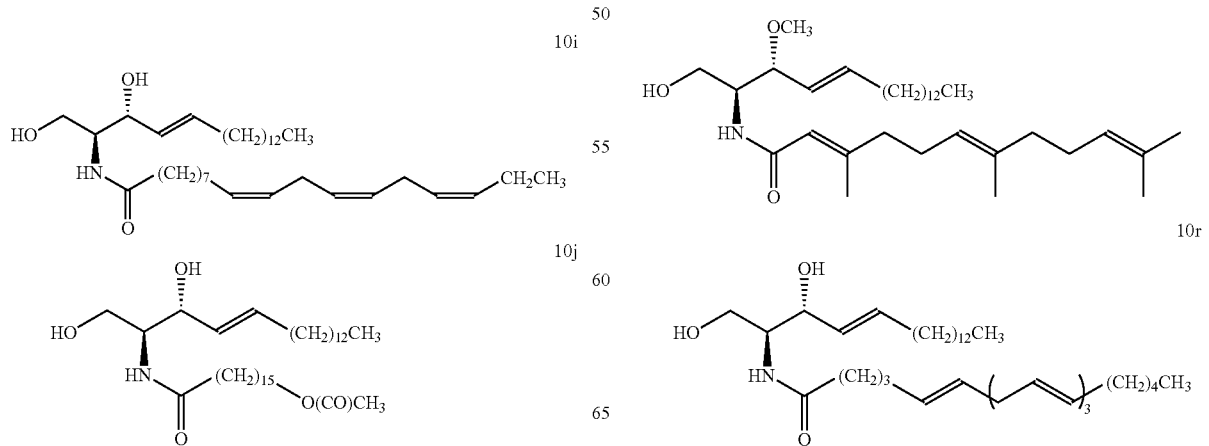

-continued

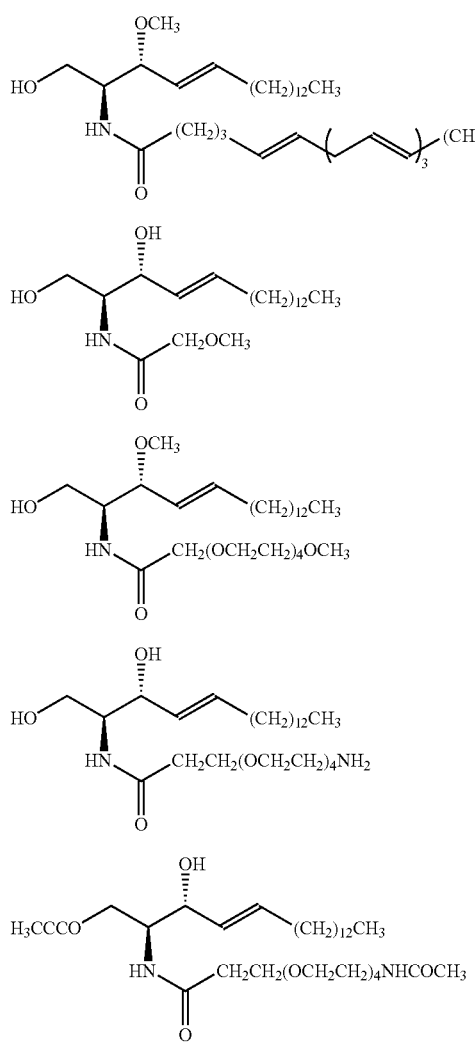

There are several structural features that impart particularly advantageous disrafting properties to sphingosine derivatives. These structural features can be present alone or in combination in a preferred compound.

One of these features is the presence of a bulky group attached to the X group of sphingosine derivatives having formula 1. Upon incorporation of sphingosine derivatives bearing a bulky group, it is assumed that the structure of the raft is disturbed, which may lead to a modulation of the biological function. Examples for disrafters that could act via this mechanism are those sphingosine derivatives listed above in which $R^4$ is 1-adamantyl, (1-adamantyl)methylene or (1-adamantyl)ethylene. Another group of derivatives that may act via this mechanism are those sphingosine derivatives listed above in which $R^4$ is a $C_{3-8}$ cycloalkyl ring optionally substituted by one or more $C_{1-4}$ alkyl groups or halogens; a ($C_{3-8}$ cycloalkyl)methylene group, wherein the cycloalkyl ring is optionally substituted by one or more $C_{1-4}$ alkyl groups or halogens; or a [2-($C_{3-8}$ cycloalkyl)]ethylene group, wherein the cycloalkyl ring is optionally substituted by one or more $C_{1-4}$ alkyl groups or halogens. Alternative derivatives representing this mode of action are sphingosine derivatives in which $R^4$ is a branched hydrocarbon as exemplified by geranyl or farnesyl residues attached to the 2-amino group.

A second structural feature is the presence of one or more polar groups in one of the lipophilic side chains of the sphingosine derivative resulting in an overall amphiphilic structure of the side chain. Upon incorporation of this type of sphingosine derivative into a raft, the amphiphilic side chains are believed to disturb the raft structure, which may result in a modulation of its function. Examples for disrafters that could act via this mechanism are those sphingosine derivatives listed above in which $R^4$ is the group of formula 2.

A third structural feature is the presence of cis double bonds in one of the lipid side chains of the sphingosine derivative. The presence of cis double bonds reduces the flexibility and causes deviation from the extended conformation of the lipid side chains. Upon incorporation of this type of sphingosine derivative into a raft, the non-flexible and non-linear side chains are believed to disturb the raft structure, which may result in a modulation of its biological function. Examples for disrafters that could act via this mechanism are those sphingosine derivatives listed above in which $R^4$ is a $C_{6-30}$ hydrocarbon group including one or more cis double bonds, wherein one or more hydrogens are optionally replaced by halogen.

A fourth structural feature that is believed to enhance the disrafting properties of sphingosine derivatives is an overall "cone shape" of the molecule. This can be achieved by incorporating a long and a short lipid side chain into the sphingosine derivative. For example, while $R^3$ could be a long chain, such as $C_{9-25}$ alkyl, $R^4$ could be a short chain, such as a $C_{1-5}$ hydrocarbon group, wherein one or more hydrogens are optionally replaced by halogen.

Ceramide derivatives having formula 1 in which X is NHCO can be easily prepared by reaction of a sphingosine base, which can be obtained with backbones of various length as reviewed by Koskinen (P. M. Koskinen, A. M. P. Koskinen, Synthesis 1998, 1075 and literature cited therein), and suitable carboxylic acids under standard peptide coupling conditions. A wide variety of suitable carboxylic acid building blocks are commercially available. Moreover, carboxylic acid building blocks containing an oligoglycolic group are either commercially available or their synthesis can be achieved as described by F. Vögtle (F. Vögtle, U. Heimann, Liebigs Ann. Chem. 1980, 858-862). The corresponding alkoxy(poly-1,3-propylene)acetic acid building blocks can be obtained by reduction of commercially available methoxypropionic acid methyl ester, followed by O-alkylation with ethyl 3-bromopropionate and subsequent saponification. Successive reduction/alkylation cycles can yield building blocks of increased chain lengths. Mono-, bis- and tris-1,2-propyleneglycol monoethyl ethers are commercially available. Their alkylation with bromoacetate and subsequent saponification can provide the corresponding carboxylic acid building blocks.

Ureas and carbamates having formula 1 in which X is NHCONH and NHCO$_2$, respectively can be formed by reaction of the corresponding isocyanates, which can be prepared from sphingosine derivatives, and alcohols or amines. These alcohols and amines can be easily obtained from the carboxylic acids by procedures well known in the art.

In contrast, compounds having formula 1, wherein X is NH, can be provided by simple alkylation strategies with suitable precursors derived from the corresponding carbinols, which themselves are either commercially available or can be obtained from the corresponding carboxylic acids.

Compounds having formula 1 in which X is NHSO$_2$ can be synthesized by reaction of sphingosine bases with various sulfonyl chlorides, which can be formed via sulfonation of the corresponding alkyl or alkenyl halides (E. E. Gilbert, *Sulfonylation and Related Reactions*, Interscience, New York, 1965, pp. 136-148, 161-163) followed by transformation into sulfonyl chlorides.

Compounds 10a, 10b, 10c and 10d are commercially available.

Compounds 10e and 10f can be obtained by amide formation under standard peptide coupling conditions using $C_{18}$-sphingosine as a substrate and commercially available 4-tert-butylcyclohexyl carboxylic acid and 1-adamantyl carboxylic acid as reagents, respectively. The C18-sphingosine is prepared as described in the literature (A. H. Merrill, Y. A. Hannun (Eds.), *Methods in Enzymology*, Vol. 311, Academic Press, 1999; P. M. Koskinen, A. M. P. Koskinen, *Synthesis* 1998, 1075).

In a similar fashion compound 10g can be prepared by reaction of $C_{18}$-sphingosine with 3,6,9,12,15-pentoxahexadecanoic acid, which is available in two steps from commercially available tetraglycolmonomethyl ether by ethyl diazoacetate alkylation and subsequent saponification.

Compound 10h can be obtained by N-acylation of $C_{18}$-sphingosine using 2-(2-methoxyethoxy)acetic acid, which can be prepared as described in the literature from commercially available ethyleneglycol monomethyl ether and ethyl diazoacetate followed by saponification of the resulting ethyl ester (R. B. Dyer, D. H. Metcalf, R. G. Ghirardelli, R. A. Palmer, E. M. Holt, *J. Am. Chem. Soc.* 1986, 108, 3621-3629).

Compounds 10i, 10p, 10q, 10r and 10s can be prepared by N-acylation of either $C_{18}$-sphingosine (as for 10i, 10p and 10r) or 3-methoxy-substituted $C_{18}$-sphingosine (as for 10q and 10s) with linolenic acid, farnesoic acid or arachidonic acid, respectively.

Compounds 10j, 10k, 10m, 10u, 10v, 10w and 10x can be prepared in a similar fashion by N-acylation of suitable sphingosine derivatives with the corresponding carboxylic acid precursors, wherein the syntheses of compounds 10j and 10x may involve additional acetylation of selected hydroxy or amino functions.

Finally, compounds 10n and 10o can be prepared by lithium aluminum hydride reduction of the corresponding ceramide precursors.

In accordance with the data and information provided herein the present invention provides in particular for the use of the sphingolipid derivatives in a medical setting for the treatment of human as well as animal disorders and diseases which are characterized by biological processes taking place in or on lipid rafts. As will be detailed herein below, these diseases and/or disorders comprise, for example neurodegenerative disorders like Alzheimer's disease or prion-related diseases/disorders, Creutzfeldt-Jakob disease, Kuru, Gerstmann-Sträussler-Scheinker syndrome and fatal familial insomnia (FFI) as well as infectious diseases like viral, bacterial or parasite infections. Furthermore and as documented in the appended examples immunological and/or allergic disorders may be ameliorated, prevented or treated by the compounds provided herein. These disorders comprise, in particular hyperallergenic disorders (asthma), autoimmune diseases (like Batten disease), systemic lupus erythematosus or arteriosclerosis. Further disorders like proliferative disorders (cancer) and systemic disorders like diabetes are considered valuable targets to be treated by the compounds provided herein. Of particular interest in this context are, however, infectious diseases (preferably viral and bacterial diseases, most preferably influenza infections) as well as the immunological or hyperallergenic disorders, like asthma.

Prior to investigating the inhibitory activity of compounds given in the present invention in various biological assays, said compounds may also be evaluated in several toxicity assays in order to document their safety in the concentration range used or to determine their highest non-toxic concentration. Thus, it can be assured that observed inhibitory effects in each disease-relevant assay are not due to toxic effects exerted by the compound under evaluation. Toxicity assays are well known in the art and may, inter alia, comprise lactate dehydrogenase (LDH) or adenylate kinase (AK) assays or an apoptosis assay. Yet, these (cyto)-toxicity assays are, as known by the skilled artisan, not limited to these assays. The following assays are, accordingly, non-limiting examples.

The release of lactate dehydrogenase (LDH) from cultured cells exposed to a substance provides a sensitive and accurate marker for cellular toxicity in routine biocompatibility testing in vitro (Allen, *Promega Notes Magazine* 45 (1994), 7). Promega's commercial CytoTox-ONE™ LDH assay kit (Promega # G7891) represents a homogeneous membrane integrity assay combined with a fluorometric method for estimating the number of nonviable cells present in multiwell plates.

The assay may be performed according to the manufacturer's instructions (Promega Technical Bulletin No. 306) in triplicate wells for each compound concentration. The incubation period is 16 h for MDCK cells and 1.5 h for RBL cells, corresponding to the exposure time in the assays for which the LDH assay serves as reference (focus reduction assay and degranulation assay). Solvent controls may be done only at the highest solvent concentration.

A maximum assay readout can be provided by adding detergent to three wells of the 96-well plate (as described in the Promega protocol). The background can consist of wells without cells. Each well may be processed and calculated independently, so that each plate contains the necessary controls. Triplicate readings are averaged, the average background subtracted and the resulting value converted to %maximum. A threshold of toxicity may be defined as follows: for MDCK cells the threshold may be defined as twice the percentage of untreated or solvent-treated controls.

If the result at a certain compound concentration is below threshold, this concentration may be deemed non-toxic. The highest non-toxic concentration, the maximal tolerated concentration, dose, may be defined as the highest dose at which toxicity was not observed.

All evaluations of compounds in assays described herein can be processed at the maximal tolerated concentration as determined in the LDH release assay or below.

In a second assay, the release of the enzyme adenylate kinase (AK) from damaged cells is measured. AK, a robust protein present in all eukaryotic cells, is released into the culture medium when cells die. The enzyme phosphorylates ADP to generate ATP, which is measured using the bioluminescent firefly luciferase reaction.

After 18 h and 48 h incubation time 20 μL of the supernatant of each well is transferred into new plates and the ToxiLight assay (Cambrex) is performed according to the manufacturer's instructions (ToxiLight, Cambrex Bio Science, Rockland, USA, cat# LT07-117). After the conversion of added ADP to ATP by the adenylate kinase, luciferase catalyses the formation of light from ATP and luciferin in a second step. The luminescence measurements are performed with a Genios Pro instrument (TECAN).

This assay may be performed prior to the SV40 assay described in the experimental part in order to confirm that observed inhibition is not due to compound-induced damage of the cells.

In a third assay, the induction of apoptosis exerted by the compounds provided in the present invention is evaluated. Loss of the phospholipid asymmetry of the cell membrane represents one of the earliest cellular changes of the apoptotic process (Creutz (1992) Science 258, 924). Annexins are ubiquitous homologous proteins that bind phospholipids in the presence of calcium. As the movement of phosphatidylserine from the internal leaflet to the external leaflet of the phospholipids bilayer represents an early indicator of apoptosis, annexin V and its dye conjugates can be used for the detection of apoptosis because they interact strongly and specifically with the exposed phosphatidylserine (Vermes (1995) J. Immunol. Methods 184, 39).

The assay may be performed according the manufacturer's instructions (Annexin V Conjugates for Apoptosis Detection, Molecular Probes, cat# A13201). After 72 h incubation time DRAQ5™ is added to the cells at a final concentration of 5 µM. After 1 h incubation time the medium was discarded and AnnexinV conjugated to Alexa Fluor 488 (Alexa488; Molecular Probes) is added (250 ng per mL). After incubation and washing, the cells are fixed with paraformaldehyde and a microscopic analysis with an OPERA automated confocal fluorescence microscope (Evotec Technologies GmbH) is performed using 488 and 633 nm laser excitation and a water-immersion 10-fold objective. Four images per well can be taken automatically, the total number of cells (DRAQ5) and the area of AnnexinV-Alexa488 can be determined by automated image analysis and average and standard deviations for triplicates may be calculated. The apoptotic index can be calculated by dividing the area of AnnexinV (pixels) with the total number of nuclei (DRAQ5 stained), multiplied by 100%. The result can be expressed as a comparison to untreated cells after normalization to the background (solvent-treated cells).

This assay can also be performed prior to the SV40 assay described below in order to confirm that observed inhibition is not a consequence of the induction of apoptosis subsequent to compound addition.

Finally, by visual evaluation of cell morphology during assay operation using a light microscope evidence of toxic effects caused by the tested compounds can be assessed.

In the following more detailed information on diseases and disorders are given. These diseases and disorders may be prevented, ameliorated or treated by using the compounds provided herein. Compounds provided herein are particularly useful in this medical context, with the compounds shown in formulae 10a, 10b, 10c, 10e, 10f, 10g, 10h, 10i, 10j, 10k, 10l, 10n, 10o, 10p, 10q, 10r, 10u, 10v, 10w and 10x being particularly preferred. In particular, the experimental data provided herein document that 10a, 10b, 10c, 10e, 10f, 10g, 10h, 10i, 10j, 10k, 10l, 10n, 10o, 10p, 10q, 10r, 10u, 10v, 10w and 10x are particularly preferred compounds in distinct medical interventions or preventions. Without being bound by theory, in some cases mechanistic models are given how the compounds described herein may function.

Alzheimer disease (AD) depends on the formation of amyloid plaques containing the amyloid-beta-peptide (Aβ), a fragment derived from the large type I transmembrane protein APP, the amyloid precursor protein. The Aβ fragment is cleaved sequentially by enzymes termed beta-secretase (BACE) and gamma-secretase. BACE is an aspartyl-protease that cleaves APP in its luminal domain, generating a secreted ectodomain. The resulting 10-kDa C-terminal fragment is subsequently cleaved by gamma-secretase, which acts at the transmembrane domain of APP, thus releasing Aβ. A third enzymatic activity, the alpha-secretase, counteracts the activity of BACE by cleaving APP in the middle of the Aβ region, yielding products that are non-amyloidogenic: The beta fragment (a secreted ectodomain) and the short C-terminal stub that is also cleaved by beta-secretase. Therefore, alpha-cleavage directly competes with beta-cleavage for their common substrate APP. Lipid rafts play a role in regulating the access of beta-secretase to the substrate APP. The compounds provided herein are supposed to disrupt lipid rafts and, thereby to inhibit beta-secretase cleavage. Without being bound by theory, this may be achieved either by 1) interfering with the partitioning of APP and BACE in rafts, 2) the intracellular trafficking of APP and BACE to meet within the same rafts and 3) the activity of BACE in rafts, to inhibit Aβ fragment production and generation of Alzheimer disease.

Also prion disorders may be treated and/or ameliorated by the medical use of the compound provided herein. A conformational change resulting in amyloid formation is also involved in the pathogenesis of prion disease. Prion diseases are thought be promoted by an abnormal form (PrPsc) of a host-encoded protein (PrPc). PrPsc can interact with its normal counterpart PrPc and change the conformation of PrPc so that the protein turns into PrPsc. PrPsc then self-aggregates in the brain, and these aggregates are thought to cause the disorders manifested in humans as Creutzfeldt-Jakob disease, Kuru, Gerstmann-Sträussler-Scheinker syndrome, or fatal familial insomnia (McConnell, Annu. Rev. Biophys. Biomol. Struct. 32 (2003), 469-492). The mechanism by which PrPc is converted to PrPsc may involve lipid rafts. PrP is a GPI-anchored protein. Both PrPc and PrPsc are associated with DRMs in a cholesterol-dependent manner. The GPI anchor is required for conversion. When the GPI anchor is replaced by a transmembrane domain, conversion to abnormal proteins is blocked. In vitro, the conversion of PrPc to PrPsc, as monitored by PrP protease resistance, occurs when microsomes containing PrPsc are fused with DRMs containing PrP (Baron (2003) J. Biol. Chem. 278, 14883-14892; Stewart (2003) J. Biol. Chem. 278, 45960-45968). Extraction with detergent leads to raft clustering in DRMs. Fusion of microsomes with DRMs was necessary in this experiment because simply mixing the membranes did not lead to measurable generation of new PrPsc.

Lipid rafts promote, accordingly, abnormal prion conversion. Endocytosis has also been shown to play a role for prion conversion, as is the case for BACE cleavage of APP. Rafts containing PrPc and PrPsc probably become clustered after endocytosis. It is also possible that the protein factor X, postulated to mediate conversion, is involved in raft clustering after endocytosis. If PrPc and PrPsc were clustered into the same raft platform after endocytosis, an increase of interaction efficiency would result and lead to amplification of conversion. Accordingly, the compounds of the invention are also useful in the treatment and/or prevention of prion diseases.

Several viruses and bacteria employ lipid rafts to infect host cells. In particular, lipid rafts are involved in the entry, assembly and egress of several enveloped viruses. As shown in the appended technical examples, influenza virus is a prototype of such a virus.

The compounds described in this invention (disrafters) can be applied to 1) disrupt rafts and interfere with the transport of hemagglutinin and neuraminidase to the cell surface, 2) prevent the clustering of rafts containing the spike glycoproteins induced by M proteins and, thus, interfere with virus assembly, 3) by increasing the size/volume of lipid rafts or 4) prevent the fission of the budding pore (pinching-off) which occurs at the phase border of raft (viral membrane) and non-raft (plasma membrane). Preferred compounds in this regard are 10b, 10e, 10f, 10g, 10h, 10i, 10j, 10p, 10q, 10r, 10k, 10n, 10o, 10u, 10v and 10w, while compounds 10b, 10g, 10h, 10l, 10j, 10p, 10q, 10r, 10k, 10n, 10o, 10u, 10v and 10w are particularly preferred. Even more preferred compounds are 10b, 10g, 10h, 10j, 10u and 10v. Corresponding experimental evidence is provided in the appended examples. It is of note that also further data, e.g. provided in the SV40 assay described herein, showed good inhibitory effects, in particular compound 10a.

In viral infection, raft clustering is involved in the virus assembly process. Without being bound by theory, sphingosine derivatives with a weak hydrophobic packing potential would be expected to inhibit raft clustering. Similarly, molecules with an affinity to the liquid ordered phase but unable to contribute to its condensation, such as single-chain (lyso)lipids, would weaken packing interations.

For example, $C_2$-dihydroceramide (10b) despite its lipophilicity, may induce a certain amount of disorder due to its unsymmetrical shape compared to natural raft components such as C16-ceramide, without complete disruption of the membrane. Bulky, lipophilic substituents attached to the 2-amino function in compounds 10e and 10f provide for the same result, though in those cases the increased sterical demand is thought to be causative for raft disorder.

A similar effect may result from the substitution pattern of compounds 10i, 10p and 10r, wherein accumulated cis-double bonds (as in 10i), a combination of trans-double bonds with methyl substituents (as in the farnesyl rest of 10p) or an accumulation of four non-conjugated trans-double bonds (as in 10r) are thought to lead to a diminished packing potential of the hydrocarbon substructures after intercalation into the lipophilic phase of the raft domain.

In an alternative concept, reduction of the hydrogen bond donor capacity inside the polar headgroup of sphingosine derivatives also leads to weaker packing of such structures within lipid raft domains, as exemplified in structures 10q and 10k. A key feature in those structures is the 3-methoxy substituent combined with the afore mentioned farnesyl residue (as in 10q) or a shorter hexanoyl substituent at position 2 (as in 10k), thus leading to decreased packing potential due to decreased symmetry.

Strengthening the hydrogen bonding capacity at position 2 represents another principle to derive compounds with high potency. In compounds 10n and 10o the amide function at position 2 is reduced to an amine leading to increased raft disruption which results in enhanced inhibition of viral replication, though to a slightly lesser extent than observed with the structures described above.

Introduction of a polar group at the end of a long, symmetrical side chain at position 2 represents another structural feature leading to even more preferred moieties. The polar acetate group in compound 10j might prevent the introduction of that position deeply into the lipid phase of raft domains, thus resulting in a bent conformation displaying a U-shape and leading to a strongly decreased packing potential. Similar effect may be present in compounds 10g, 10h, 10u, 10v and 10w, whose ether-derived side chains represented by generic formula 2 might cause significantly increased disorder when incorporated into lipid raft domains.

In particular, a combination of such polyether side chains with the above-described 3-methoxy substitution, as seen in compound 10v, results in a maximized effect as indicated by very effective inhibition of the viral reproduction.

The described structural features leading to the presented inhibition of viral reproduction provide the above mentioned compounds as suitable candidates for the development of pharmaceuticals for the treatment of influenza infection as shown in the experimental part.

As the mechanism of virus release for HIV-1 is similar to that of influenza virus, with respect to raft involvement, the above compounds can also be developed for the treatment of AIDS. To demonstrate this, compounds were tested for inhibition of infection of HeLa TZM cells by the HIV-1 strain NL4-3 (laboratory adapted B-type strain) as a disease model for AIDS. A particular preferred compound to this end is compound 10a. Thus, a short hexanoyl side chain attached to position 2 of the sphingosine core structure resulting in an unsymmetrical shape of the lipophilic substructure of the molecule represents a particular preferred structural pattern for the pharmaceutical intervention in the case of HIV infection. As shown in the same experimental setting, other preferred compounds are 10v, 10w and 10x. The common structural feature of those compounds is the polyether side chain comprising at least four glycolic units, wherein the attachment of an additional polar function at the end of such polyether chain results in even increased potency, as demonstrated in the case of 10x. Corresponding evidence is provided in the experimental part.

Further viral diseases (as non limiting examples) which may be approached with the above compounds or derivatives thereof are herpes, ebola, enterovirus, Coxsackie virus, hepatitis C, rotavirus and respiratory syncytial virus. Accordingly, particularly preferred compounds as well as preferred compounds provided herein in the context of a specific (viral) assay or test system may also be considered useful in the medical intervention and/or prevention of other infectious diseases, in particular viral infections.

As detailed herein, the compounds which are active in the disruption of lipid rafts in cells infected with influenza virus or in the SV40 assay may also be employed in other medical settings, in particular in other viral infection, most preferably in HIV infections. It is also envisaged that compounds shown to be useful in AIDS intervention/HIV infection are of use in further infectious diseases, like other viral infections.

Herpes simplex virus (HSV) entry requires the interaction of viral glycoproteins with a cellular receptor such as herpesvirus entry mediator (HVEM or HveA) or nectin-1 (HveC). During HSV infection, a fraction of viral glycoprotein gB associates with lipid rafts, as revealed by the presence in detergent-resistant membranes (DRM). Disruption of lipid rafts via cholesterol depletion inhibits HSV infection, suggesting that HSV uses lipid rafts as a platform for entry and cell signalling (Bender). The rafts-disrupting agents of the invention may be employed in the inhibition of the partitioning of either viral glycoproteins or an interacting molecule into rafts as a strategy to inhibit infection and replication of HSV.

Also Ebola virus assembly and budding depends on lipid rafts. These functions depend on the matrix protein VP40 that forms oligomers in lipid rafts. The use of compounds described in this invention leads to a disruption of lipid rafts. This may be used as a means to inhibit VP40 oligomerization and, consequently, Ebola virus infection and assembly.

Enteroviruses use the complement regulatory protein decay-accelerating factor (DAF), a GPI-anchored protein, as a receptor to infect cells. Like other GPI-anchored proteins, DAF partitions to lipid rafts. Consistently, viruses infecting the cell via this receptor system depend on lipid rafts. In particular, lipid rafts appear to be essential for virus entry, after binding to the cell surface. Furthermore, viruses using the DAF receptor system copurify with lipid raft components in a DRM extraction assay. Since lipid rafts enable enteroviruses to enter cells, compounds as disclosed in this invention that disrupt lipid rafts or the partitioning of DAF to lipid rafts or the post-binding events leading to cell infection, can be used for the prevention and treatment of enterovirus-based disorders.

Coxsackie virus entry and cell infection depend on lipid rafts. Receptor molecules (integrin αvβ3 and GRP78) accumulate in lipid rafts following Coxsackie virus infection. The raft-disrupting compounds of the invention disrupt lipid rafts or the partitioning of Coxsackie virus receptors to lipid rafts or the post-binding events leading to cell infection and may, accordingly, be used for the prevention and treatment of Coxsackie virus-based disorders (as well as in disorders caused by viruses, similar to Coxsackie virus.

Rafts are also implicated in the life cycle of Human Immunodeficiency Virus (HIV) and, accordingly, in AIDS. Without being bound by theory, disrafters of the present invention can be applied to disrupt rafts and interfere with the transport of HIV glycoproteins to the cell surface, prevent the clustering of rafts containing the spike glycoproteins induced by Gag proteins and, thus, interfere with virus assembly. Accordingly, the compounds described herein are also medically useful in the treatment and amelioration of HIV-infections and AIDS. As mentioned herein above, preferred compounds in this context are compounds which are qualified as "disrafters" in accordance with this invention and which show positive results in the appended "influenza assay" which is an assay for testing the efficacy of a compound described herein. Compounds which show positive results in the appended "influenza assay", may, accordingly, also be employed in the treatment, prevention and/or amelioration of other vial infections, like HIV-infections (and AIDS).

Lipid rafts are also involved in the infectious cycle of hepatitis C virus (HCV). The compounds described in this invention as "disrafters" may disrupt lipid rafts or the partitioning of proteins constituents of viral replication complex to lipid rafts or interfere with the replication events leading to virus assembly. Accordingly, the compounds described herein are also useful in the prevention and treatment of hepatitis, in particular of hepatitis C.

Rotavirus cell entry depends on lipid rafts. Molecules implicated as rotavirus receptors such as ganglioside GM1, integrin subunits α2β3, and the heat shock cognate protein 70 (hsc70) are associated with lipid rafts. Furthermore, rotavirus infectious particles associate with rafts during replication and lipid rafts are exploited for transport to the cell surface. The compounds described herein may be employed to disrupt lipid rafts or the partitioning of receptors for Rotavirus, the formation of protein and lipids complexes necessary for replication and transport via lipid rafts. Accordingly, they are useful in the prevention and treatment of Rotavirus infection.

Simian virus 40 (SV40) enters cells via an atypical caveolae-mediated endocytic pathway rather than via clathrin-coated pits, (Anderson (1996) Mol. Biol. Cell 7, 1825-1834; Stang (1997) Mol. Biol. Cell 8, 47-57). This mechanism of cellular uptake is also employed by members of the virus family Coronaviridae, which are the responsible pathogens causing human diseases such as severe acute respiratory syndrome (SARS) and upper respiratory tract infections, and by the respiratory syncytial virus (Macnaughton (1980) J. Clin. Microbiol. 12, 462-468; Nomura (2004) J. Virol. 78, 8701-8708; Drosten (2003) N. Engl. J. Med. 348, 1967-1976; Ksiazek (2003) N. Engl. J. Med. 348, 1953-1966). Moreover, bacteria also use this mechanism for cellular uptake, e.g. *Mycobacterium* spp. which cause tuberculosis. Thus, the herein presented SV40 assay serves as model for caveolae-mediated cellular uptake, and the compounds described in the present invention may be used for pharmaceutical intervention in the case of diseases caused by the above described viruses and bacteria.

Uptake of Simian Virus 40 (SV40) into caveolae rafts is a model for infection by diverse bacteria and viruses which utilize the raft to gain entry to the cell (Pelkmans (2002) Science 296, 535-539). The assay is used as a screen for compounds which may inhibit bacterial or viral infection at the stage of caveolar incorporation, endocytosis and early intracellular trafficking. This mechanism is particularly relevant to infection by respiratory syncytial virus, coronavirus (e.g. SARS) and to bacterial infection by *Mycobacterium* spp., leading to tuberculosis. Accordingly, compounds which show positive results in the appended SV40 assay may also be used in the context of medical intervention of infections of the respiratory tract, like tuberculosis and bacterial infestation by, but not limited to, *Campylobacter* spp., *Legionella* spp., *Brucella* spp., *Salmonella* spp., *Shigella* spp., *Chlamydia* spp., FimH and Dr+*Escherichia coli*.

The compounds presented herein are suitable to inhibit such uptake by a caveolae-mediated mechanism as demonstrated by the SV40 assay using HeLa cells infected with wild type SV40 viruses. Moreover, the lack of inhibition in a similar assay using Vesicular Stomatitis Virus (VSV) demonstrates the capability of this working hypothesis, as VSV enters via clathrin-mediated endocytosis into early and late endosomes. In this context, compound 10a represents a particular preferred embodiment for the pharmaceutical intervention in the case of viral and/or bacterial infections.

As pointed out above, the compounds described herein may also be employed in the treatment or amelioration of bacterial infections and toxicoses induced by secreted bacterial toxins.

Bacterial toxins such as cholera (from *Vibrio cholerae*), aerolysin (*Aeromonas hydrophilia*), anthrax (*Bacillus anthracis*) and helicobacter toxin form oligomeric structures in the raft, crucial to their function. The raft is targeted by binding to raft lipids such as ganglioside GM1 for cholera. Prevention of oligomerization is equivalent to prevention of raft clustering, hence the same or similar compounds as those used for viral infection should be able to inhibit the activity of bacterial toxins. However, a difference in dosing regimen would be expected as toxins will be rapidly cleared from the blood and treatment may be short in comparison to viral infection where a course of treatment may be necessary.

In bacterial infection such as tuberculosis, shigellosis and infection by *Chlamydia* and uropathogenic bacteria the organism is taken up into the cell in a raft-dependent internalization process often involving caveolae. Prevention of localization of the bacterial receptor in rafts or blockage of internalization would prevent infection.

Tuberculosis is an example of a bacterial infectious disease involving rafts. First, Complement receptor type 3 (CR3) is a receptor able to internalize zymosan and C3bi-coated particles and is responsible for the non-opsonic phagocytosis of *Mycobacterium kansasii* in human neutrophils. In these cells CR3 has been found associated with several GPI-anchored proteins localized in lipid rafts of the plasma membrane. Cholesterol depletion markedly inhibits phagocytosis of *M. kansasii*, without affecting phagocytosis of zymosan or serum-opsonized *M. kansasii*. CR3, when associated with a GPI protein, relocates in cholesterol-rich domains where *M. kansasii* are internalized. When CR3 is not associated with a GPI protein, it remains outside of these domains and mediates phagocytosis of zymosan and opsonized particles, but not of *M. kansasii* isopentenyl pyrophosphate (IPP), a mycobacterial antigen that specifically stimulates Vgamma9Vdelta2 T cells. Accordingly, the present invention also provides for the use of the compounds disclosed herein in the treatment and/or amelioration of an *Mycobacterium* infection, preferably of a *Mycobacterium tuberculosis* infection.

Shigellosis is an acute inflammatory disease caused by the enterobacterium *Shigella*. During infection, a molecular complex is formed involving the host protein CD44, the hyaluronan receptor, and the *Shigella* invasin IpaB, which partitions during infection within lipid rafts. Since raft-dependent interactions of host cellular as well as viral proteins are required for the invasion process, the compounds described herein may be employed to disrupt lipid rafts or the partitioning of receptors for *Shigella*, the partitioning of *Shigella* proteins, the formation of protein and lipids complexes necessary for replication and transport via lipid rafts. Therefore, the invention also provides for the medical/pharmaceutical use of the compounds described herein the treatment or amelioration of shigellosis.

*Chlamydia pneumoniae*, an important cause of respiratory infections in humans that additionally is associated with cardiovascular disease, *Chlamydia psittaci*, an important pathogen in domestic mammals and birds that also infects humans, as well as other *Chlamydia* strains (*C. trachomatis* serovars E and F), each enter host cells via lipid rafts.

The compounds of the invention may be used to disrupt lipid rafts or the partitioning of protein and lipids complexes necessary for replication and transport via lipid rafts, can be used for the prevention and treatment of *Chlamydia* infection, in particular *C. pneumonia* infections.

Type 1 fimbriated *Escherichia coli* represents the most common human uropathogen, that invades the uroepithelium despite its impermeable structure, via lipid rafts-dependent mechanisms.

The compounds provided herein may disrupt lipid rafts or caveolae, the partitioning of protein and lipids complexes necessary for the binding of *E. coli*, transport via lipid rafts and subsequent infection across the bladder and similar epithelia. Therefore, the compounds described in the invention may be used for the prevention and treatment of bacterial infectious diseases, in particular uropathologies.

Various bacterial toxins exploit rafts to exert their cytotoxic activity. For example, the pore-forming toxin aerolysin, produced by *Aeromonas hydrophila*, on mammalian cells binds to an 80-kD glycosyl-phosphatidylinositol (GPI)-anchored protein on BHK cells and partitions in rafts. The protoxin is then processed to its mature form by host cell proteases. The preferential association of the toxin with lipid rafts increases the local toxin concentration and thereby promotes oligomerization, a step that it is a prerequisite for channel formation. Accordingly, the compounds described herein are also useful in the treatment, prevention or amelioration of a disease related to a bacterial infection. In context of this invention, it is also envisaged that the compounds described herein are employed in co-therapy approaches. Accordingly, it is also envisaged that the compounds are administered to a patient in need of treatment in combination with further drugs, e.g. antibiotics.

The protective antigen (PA) of the anthrax toxin binds to a cell surface receptor and thereby allows lethal factor (LF) to be taken up and exert its toxic effect in the cytoplasm. Clustering of the anthrax toxin receptor (ATR) with heptameric PA or with an antibody sandwich causes its association to specialized cholesterol and glycosphingolipid-rich microdomains of the plasma membrane (lipid rafts). Altering raft integrity using drugs prevented LF delivery and cleavage of cytosolic MAPK kinases.

"Disrafters" as disclosed herein may be applied to disrupt rafts and interfere with the clustering/oligomerization of toxins. Accordingly, the compounds of the invention are also useful in the treatment/prevention of an infection with *Bacillus anthracis*.

*Helicobacter pylori* has been implicated in the generation of chronic gastritis, peptic ulcer, and gastric cancer. Lipid rafts play a role in the pathogenetic mechanisms of *Helicobacter pylori* intoxication. Therefore, the compounds described herein are also useful in the treatment, prevention or amelioration of a *Helicobacter* infection, e.g. the treatment of gastritis, peptic ulcers and/or gastric ulcers.

The compounds described herein are also useful in the treatment/prevention of an infection with *plasmodium*, in particular *P. falciparum*. Accordingly, the compounds described herein may be employed to disrupt lipid rafts or caveolae, the partitioning of protein and lipids complexes necessary for the binding of *Plasmodium falciparum* to red blood cells, or the transport via lipid rafts and subsequent infection. Therefore, they may be used for the prevention and treatment of malaria.

Also asthma and other immunological diseases may be treated by the use of the compounds as disclosed herein. Preferred compounds in this context are compounds 10c, 10g, 10h, 10l, 10u, 10v or 10w, with compounds 10c, 10l, 10v, and 10w being more preferred, and compound 10w being particularly preferred. The cells used most intensively to study the role of lipid rafts in FcεRI-mediated signaling are rat basophilic leukemia (RBL) cells. A role for rafts in the interactions that follow FcεRI aggregation, mainly in signaling complexes assembled around the linker for activation of T cells (LAT), is described (Metzger, Mol. Immunol. 38 (2002), 1207-1211).

The compounds as described herein may be applied to disrupt rafts and 1) interfere with the transport and aggregation of FcεRI at the cell surface, 2) interfere with the transport and aggregation of rafts by LAT at the cell surface. Accordingly, the invention also provides for the use of the compounds disclosed herein in the treatment/prevention of asthma. The compounds described herein provide positive results in a cell based assay (degranulation assay) which is an assay for testing substances useful in immunological as well as auto-immunological disorders.

A particular preferred compound for such treatment is compound 10c which inhibits the release of β-hexosaminidase used as marker in the degranulation assay efficiently. Thus, as exemplified with C2-ceramide 10c, the almost complete removal of the long lipophilic side chain at position 2 of the sphingolipid headgroup by acetyl capping of the 2-amino function, thus resulting in a strongly asymmetric shape of the lipophilic substructure of the molecule, represents a particular preferred substitution pattern for the pharmaceutical intervention in the case of immunological diseases, especially asthma. It has to be noted that to this aim, the 4,5-double bond of the ceramide backbone seems to be important for the exertion of such effect, as the weaker inhibition of C2-dihydroceramide 10b in the degranulation assay indicates.

In another preferred embodiment for the treatment of immunological disorders, in particular asthma, ceramides comprising polyether side chains at position 2 are employed. In this context, good results were obtained, for example, with compounds 10g, 10v and 10w, with compounds 10v and 10w being preferred, and compound 10w being even more preferred.

The value of 3-methoxy substitution for the development of sphingosine derivatives for the treatment of immunological disorders, e.g. asthma, is further demonstrated with compound 10l, which inhibits the degranulation process in the above described experimental setting. Consequently, compound 10l represents another preferred embodiment in the present invention for the development of pharmaceuticals against immunological disorders, in particular asthma.

Hyperallergenic responses such as asthma may result from overactivity of the immunoglobulin E receptor (Fc(eta)RI). This activity involves several raft processes which coordinate proteins and establish a long-term signalling platform. Disruption of the platform or prevention of assembly inhibits signalling. Hence similar to viral infection sphingosine derivatives with a weakened hydrophobic packing potential or molecules with an affinity to the liquid disordered phase but unable to contribute to its condensation, such as single-chain (lyso)lipids, would weaken packing interations. Additionally molecules which increase membrane bending, such as sphingosine derivatives with a short acyl group, resulting in an overall conical rather than cylindrical shape of the sphingosine derivative, may disrupt raft integrity enough to prevent efficient protein-protein interaction. N-(3,6,9,12,15-oxa-palmitoyl)-D-erythro-sphingosine and $C_2$-ceramide are strongly inhibitory in a mast cell degranulation assay and are therefore, useful for the development of anti-asthma pharmaceuticals. $C_2$-dihydroceramide is also moderately active in this assay; as documented in the appended examples.

Accordingly, also autoimmune diseases as well as hyper-allergic responses may be treated by the compounds/disrafters disclosed herein.

Neuronal ceroid lipofuscinoses, also termed Batten disease, are a heterogeneous group of autosomal recessively inherited disorders causing progressive neurological failure, mental deterioration, seizures and visual loss secondary to retinal dystrophy. The juvenile type is of special interest to the ophthalmologist as visual loss is the earliest symptom of the disorder. This occurs as a result of mutations in the CLN3 gene, encoding a putative transmembrane protein CLN3P, with no known function. CLN3P resides on lipid rafts. Therefore, the compounds described herein are useful in the treatment of, e.g., Batten disease.

Systemic lupus erythematosus (SLE) is characterized by abnormalities in T lymphocyte receptor-mediated signal transduction pathways. Lymphocyte-specific protein tyrosine kinase (LCK) is reduced in T lymphocytes from patients with SLE and this reduction is associated with disease activity. Molecules that regulate LCK homeostasis, such as CD45, C-terminal Src kinase (CSK), and c-Cbl, are localized in lipid rafts. Therefore, also SLE is a medical target for the use of the compounds disclosed in this invention.

In a further embodiment of the invention, atherosclerosis is to be treated/ameliorated or even prevented by the use of the compounds described herein in medical settings and/or for the preparation of a pharmaceutical composition.

Also proliferative disorders, like cancers may be targeted by the compounds described herein. A large number of signaling components are regulated through their partitioning to rafts. For example, the tyrosine kinase activity of EGF receptor is suppressed in rafts and cholesterol play a regulatory role in this process. Similarly, H-Ras is inactive in rafts and its signaling activity occurs upon exiting rafts. Rafts have also been shown to play a role in the regulation of apoptosis. Disrafters/compounds disclosed herein may be used in the treatment of cancer, e.g. the treatment of leukemias or tumorous diseases, as well as melanomas.

Current anti-cancer programs include the targeting of cancer cells for apoptosis. Sphingolipid derivatives described in the present invention which are capable of increasing hydrophobic interactions will lead to tighter packing of the raft, and triggering of apoptosis. Hence these compounds will be useful for development of anti-cancer agents.

A further interventional opportunity is to prevent mitogenic receptor signaling. As for immunogenic signaling, this involves the establishment of a raft based signaling platform for a ligand activated receptor. It would be expected that similar molecules to those described for immunoglobulin E receptor signaling would also inhibit mitogenic signaling.

Insulin signalling leading to GLUT-4 translocation depends on insulin receptor signalling emanating from caveolae or lipid rafts at the plasma membrane.

Accordingly, in a further embodiment of the invention, the compounds described herein may be used in the preparation of a pharmaceutical composition for the treatment of insulin-related disorders, like a systemic disorder, e.g. diabetes.

Accordingly, the compounds described in this invention are particularly useful in medical settings, e.g. for the preparation of pharmaceutical composition and the treatment, amelioration and/or prevention of human or animal diseases. The patient to be treated with such a pharmaceutical composition is preferably a human patient.

The compounds described as "disrafters" herein may be administered as compounds per se in their use as pharmacophores or pharmaceutical compositions or may be formulated as medicaments, optionally comprising pharmaceutically acceptable excipients, such as carriers, diluents, fillers, desintegrants, lubricating agents, binders, colorants, pigments, stabilizers, preservatives or antioxidants.

The pharmaceutical compositions can be formulated by techniques known to the person skilled in the art, such as the techniques published in Remington's Pharmaceutical Sciences, $20^{th}$ Edition. The pharmaceutical compositions can be formulated as dosage forms for oral, parenteral, such as intramuscular, intravenous, subcutaneous, infradermal, intraarterial, rectal, nasal, topical or vaginal administration. Dosage forms for oral administration include coated and uncoated tablets, soft gelatine capsules, hard gelatine capsules, lozenges, troches, solutions, emulsions, suspensions, syrups, elixiers, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insuflation, for example by a metered inhaler.

Dosage forms for topical administration include cremes, gels, ointments, salves, patches and transdermal delivery systems.

These pharmaceutical compositions described herein can be administered to the subject at a suitable dose. The dosage regiment will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Generally, the regimen as a regular administration of the pharmaceutical composition should be in the range of 0.1 µg to 5000 mg units per day, in some embodiments 0,1 µg to 1000 mg units per day. If the regimen is a continuous infusion, it may also be in the range of 0.1 ng to 10 µg units per kilogram of body weight per minute, respectively. Progress can be monitored by periodic assessment.

Pharmaceutically acceptable salts of compounds that can be used in the present invention can be formed with various organic and inorganic acids and bases. Exemplary acid addition salts comprise acetate, adipate, alginate, ascorbate, benzoate, benzenesulfonate, hydrogensulfate, borate, butyrate, citrate, caphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pectinate, persulfate, 3-phenylsulfonate, phosphate, picate, pivalate, propionate, salicylate, sulfate, sulfonate, tartrate, thiocyanate, toluenesulfonate, such as tosylate, undecanoate and the like. Exemplary base addition salts comprise ammonium salts, alkali metall salts, such as sodium, lithium and potassium salts; earth alkali metall salts, such as calcium and magnesium salts; salts with organic bases (such as organic amines), such as benzazethine, dicyclohexylamine, hydrabine, N-methyl-D-glucamine, N-methyl-D-glucamide, t-butylamine, salts with amino acids, such as arginine, lysine and the like.

Pharmaceutically acceptable solvates of compounds that can be used in the present invention may exist in the form of solvates with water, for example hydrates, or with organic solvents such as methanol, ethanol or acetonitrile, i.e. as a methanolate, ethanolate or acetonitrilate, respectively.

Pharmaceutically acceptable prodrugs of compounds that can be used in the present invention are derivatives which have chemically or metabolically cleavable groups and become, by solvolysis or under physiological conditions, the compounds of the invention which are pharmaceutically active in vivo. Prodrugs of compounds that can be used in the present invention may be formed in a conventional manner with a functional group of the compounds such as with an amino or hydroxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985).

The present invention also provides for a method of treatment, amelioration or prevention of disorders or diseases which are due to (or which are linked to) biochemical and/or biophysical processes which take place in, on or within lipid raft structures of a mammalian cell. Corresponding diseases/disorders are provided herein above and corresponding useful compounds to be administered to a patient in need of such an amelioration, treatment and/or prevention are also disclosed above and characterized in the appended examples and claims. In a most preferred setting, the compounds (disrafters) described herein are used in these treatment methods by administration of said compounds to a subject in need of such treatment, in particular a human subject.

Due to the medical importance of the disrafting compounds described in context of the present invention, the invention also provides for a method for the preparation of a pharmaceutical composition which comprises the admixture of the herein defined compound with one or more pharmaceutically acceptable excipients. Corresponding excipients are mentioned herein above and comprise, but are not limited to cyclodextrins. As pointed out above, should the pharmaceutical composition of the invention be administered by injection or infusion it is preferred that the pharmaceutical composition is an emulsion.

The following examples illustrate this invention.

EXAMPLES

| List of abbreviations | |
|---|---|
| DIPEA | diisopropylethylamine |
| DMAP | N,N-Dimethylaminopyridine |
| DMF | dimethylformamide |
| DMSO | Dimethylsulfoxide |
| EtOAc | ethyl acetate |
| HATU | 2-(7-aza-1H-benzotriazole-1-yl)-1,1,3,3-tetramethyluronium hexafluorophosphate |
| MeOH | methanol |
| PE | petroleum ether |
| r.t. | room temperature |
| TBAF | tetrabutylammonium fluoride |
| TBDPS | tert-butyldiphenyl silyl |
| THF | tetrahydrofurane |

General Procedures

General Procedure for the Introduction of an Acyl Side Chain

DIPEA (2.55 eq) is added to the solution of the corresponding acid (1.2 eq) and HATU (1.2 eq) in DMF/CH$_2$Cl$_2$ (1:1), and the resulting mixture is stirred at r.t. for 5 min. The solution is then added to a solution of a corresponding alcohol (1.0 eq) in CH$_2$Cl$_2$ followed by stirring at r.t. for 2 h. The reaction mixture is diluted with CH$_2$Cl$_2$ (100 mL) and washed with 1N HCl and extracted with CH$_2$Cl$_2$ (3×100 mL). The combined organic layers are dried over sodium sulfate and concentrated in vacuo. Purification of the residue by flash chromatography (silica, PE/EtOAc) yields the product.

General Procedure for the Removal of the TBDPS Group

A solution of TBAF (1M solution in THF) (4.25 eq) is added to a solution of a given TBDPS-protected ceramide (1.0 eq) in THF (15 mL), and the resulting reaction mixture is heated at 60° C. for 3 h. The reaction mixture is cooled and diluted with CH$_2$Cl$_2$ (100 mL), washed with 1N HCl and extracted with CH$_2$Cl$_2$ (3×100 mL), The combined organic layers are dried over sodium sulfate and concentrated in vacuo. Purification of the residue by flash chromatography (silica, Hexane/EtOAc/MeOH) yields the product.

Synthesis of D-Erythro-Sphingosine 2 as Key Building Block

Compound 2 was prepared from compound 1, which itself was obtained as described in the literature (Koskinen, *Synthesis* 1998, 1075).

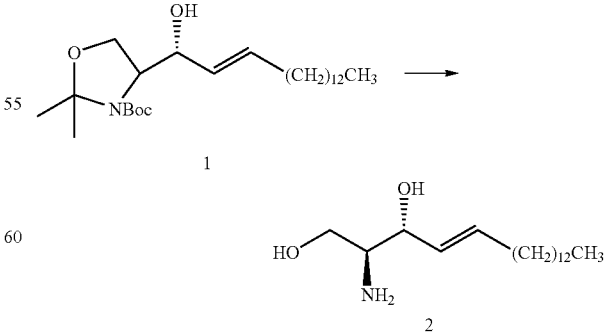

1M HCl (3 mL) was added to the solution of 1 (2.0 g, 4.5 mmol) in methanol (10 mL) and heated at reflux for 1.5 h. The reaction was cooled to room temperature and diluted with CH₂Cl₂ (100 mL), quenched with H₂O (30 mL), and a basic pH is adjusted by addition of 6M NaOH solution followed by extraction with CH₂Cl₂ (2×150 mL). The combined organic layers were dried over sodium sulfate and concentrated in vacuo. Purification of the residue by flash chromatography (silica, CH₂Cl₂/MeOH 10:1) provided 2 as white crystals (921 mg, 68%).

¹H-NMR (300 MHz, CDCl₃): δ=0.85 (t, J=6.9 Hz, 3H), 1.25 (s, 18H), 1.31 (m, 2H), 2.03 (m, 2H), 2.27 (br m, 5H), 2.92 (br m, 1H), 3.68 (m, 2H), 4.08 (m, 1H), 5.43 (m, 1H), 5.73 (m, 1H).

Synthesis of 3-TBDPS-protected D-Erythro-Sphingosine 6 as Key Building Block

Compound 6 was obtained by the following reaction sequence.

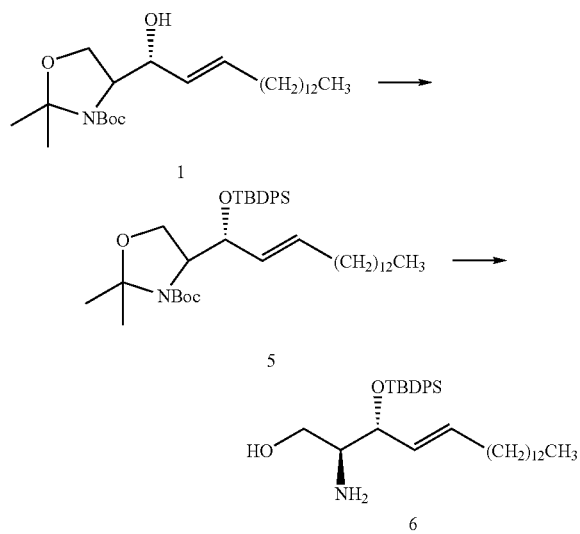

A solution of 1 (10.9 g, 24.8 mmol), imidazole (3.4 g, 50 mmol) and TBDPSCl (10.4 mL, 40 mmol) in DMF (25 mL) was stirred at 80° C. for 3 h and at 100° C. for 2 h. The reaction mixture was cooled to room temperature and quenched with H₂O (300 mL) followed by extraction with Et₂O (2×150 mL). The combined organic layers were washed with 1N HCl (100 mL) solution, saturated NaHCO₃ solution (100 mL) and H₂O (200 mL), dried over sodium sulfate and concentrated in vacuo. Purification of the residue by flash chromatography (silica, PE/EtOAc 30:1) yielded compound 5 as a colourless oil (13.7 g, 81%).

¹H-NMR (300 MHz, CDCl₃): δ=0.86 (m, 3H), 1.03 (s, 12H), 1.16 (m, 18H), 1.39 (m, 15H), 1.63 (br s, 2H), 3.85 (m, 2H), 4.12 (m, 2H), 4.90 (m, 1H), 5.18 (m, 1H), 7.34 (m, 6H), 7.61 (m, 4H).

1M HCl (25 mL) was added to a solution of 5 (13.7 g, 20.2 mmol) in 1,4-dioxane (150 mL) and heated at 100° C. for 1 h. The reaction mixture was cooled to room temperature and quenched with saturated aqueous NaHCO₃ (100 mL) followed by extraction with Et₂O (2×150 mL). The combined organic layers were washed with brine (100 mL), dried over sodium sulfate and concentrated in vacuo. Purification of the residue by flash chromatography (silica, CH₂Cl₂/MeOH 20:1) yielded 6 as a light yellow oil (7.97 g, 73%).

¹H-NMR (300 MHz, CDCl₃): δ=0.81 (m, 3H), 1.05 (s, 9H), 1.14 (m, 22H), 1.81 (m, 2H), 2.02 (br s, 3H), 2.80 (m, 1H), 3.42 (m, 1H), 3.59 (m, 1H), 4.01 (m, 1H), 5.21 (m, 2H), 7.31 (m, 6H), 7.62 (m, 4H).

Example 1

Synthesis of compound 10e: N-(trans-4-tert-butylcyclohexylcarbonyl)-D-erythro-sphingosine To a solution of 1,4-trans-4-tert-butylcyclohexanecarboxylic acid (99 mg, 0.54 mmol) and HATU (O-(7-azabenzotriazol-1-yl)-1,1,3,3-tetramethyluronium hexafluorophosphate) (205 mg, 0.54 mmol) in dimethylformamide (1.3 ml) under argon atmosphere, 1.6 M diisopropylethylamine solution in N-methylpyrrolidine (0.7 ml, 1.12 mmol) was added. After stirring at room temperature for 5 min, a solution of D-erythro-sphingosine (150 mg, 0.5 mmol) in dichloromethane (1 ml) was added. The reaction mixture was stirred for 1 h. After dilution with dichloromethane (20 ml), the reaction mixture was washed with 1 M hydrochloric acid and water and dried over sodium sulfate. The solvent was removed under reduced pressure, and the residue was subjected to chromatographic purification (silica gel, dichloromethane/methanol 10:1) to give 146 mg (63%) of the product as a light beige solid.

¹H-NMR (CDCl₃): delta=0.85 (s, 9H), 0.88 (t, 3H), 1.02 (m, 2H), 1.26 (s, 20H), 1.27-1.46 (m, 4H), 1.84-2.10 (m, 8H), 2.70 (br s, 2H), 3.69 (dd, 1H), 3.85-3.95 (m, 2H), 4.28 (m, 1H), 5.51 (dd, 1H), 5.77 (dt, 1H), 6.30 (d, 1H). MS (ESI): m/z=488 (M+Na).

Example 2

Synthesis of compound 10f: N-(1-adamantylcarbonyl)-D-erythro-sphingosine

To a solution of 1-adamantylcarboxylic acid (102 mg, 0.57 mmol) and HATU (217 mg, 0.57 mmol) in dimethylformamide (1 ml) under argon atmosphere, 1.6 M diisopropylethylamine solution in N-methylpyrrolidine (0.72 ml, 1.15 mmol) was added. After stirring at room temperature for 5 min, a solution of D-erythro-sphingosine (152 mg, 0.51 mmol) in dichloromethane (1 ml) was added. The reaction mixture was stirred for 1 h at room temperature. After dilution with dichloromethane (20 ml), the reaction mixture was washed with 1 M hydrochloric acid and water, and dried over sodium sulfate. The solvent was removed under reduced pressure, and the residue was subjected to chromatographic purification (silica gel, dichloromethane/methanol 10:1) to give 150 mg (64%) of the product as a colourless, waxy solid, which was subsequently recrystallised from methanol (1 ml).

¹H-NMR (CDCl₃): delta=0.88 (t, 3H), 1.26 (s, 20H), 1.36 (m, 2H), 1.73 (m, 6H), 1.87 (d, 6H), 2.04-2.06 (m, 5H), 2.77 (br s, 2H), 3.70 dd, 1H), 3.85-3.94 (m, 2H), 4.29 (t, 1H), 5.51 (dd, 1H), 5.78 (dt, 1H), 6.40 (d, 1H).

Example 3

Synthesis of compound 10g: N-(3,6,9,12,15-Pentoxahexadecanoyl)-D-erythro-sphingosine To a solution of 3,6,9,12,15-pentoxahexadecanoic acid (160 mg, 0.6 mmol) and HATU (228 mg, 0.6 mmol) in dimethylformamide (2 ml) under argon atmosphere, 0.8 M diisopropylethylamine solution in N-methylpyrrolidine (1.5 ml, 1.2 mmol) was added. After stirring at room temperature for 5 min, a solution of D-erythro-sphingosine (150 mg, 0.5 mmol) in dichloromethane (2 ml) was added. The reaction mixture was stirred for 1.5 h at room temperature. After dilution with dichloromethane (60 ml), the reaction mixture was washed with 1 M hydrochloric acid, with saturated aqueous sodium hydrogencarbonate solution and water. After drying over sodium sulfate, the solvent was removed under reduced pressure and the residue was subjected to chromatographic purification (silica gel, dichloromethane/methanol 20:1) to give 170 mg (62%) of the product as light yellow oil.

$^1$H-NMR (CDCl$_3$): delta=0.85 (t, 3H), 1.23 (s, 20H), 1.34 (m, 2H), 2.02 (q, 2H), 3.34 (s, 3H), 3.52 (m, 2H), 3.60-3.70 (m, 15H), 3.91 (m, 2H), 3.99 (d, 2H), 4.28 (t, 1H), 5.50 (dd, 1H), 5.75 (dt, 1H), 7.56 (d, 1H).

$^{13}$C-NMR (CDCl$_3$): delta=14.08, 22.64, 29.18, 29.21, 29.31, 29.48, 29.58, 29.61, 29.64, 31.87, 32.29, 54.52, 58.94, 62.09, 70.13, 70.25, 70.30, 70.34 (2C), 70.37 (2C), 70.45, 70.53, 70.91, 71.77, 73.96, 129.15, 133.46, 170.41. MS (ESI): m/z=570 (M+Na).

Example 4

Synthesis of compound 10h:
N-(3,6-Dioxaheptanoyl)-D-erythro-sphingosine

To a solution of 3,6-dioxaheptanoic acid (52 mg, 0.39 mmol) and HATU (148 mg, 0.39 mmol) in dimethylformamide (1 mL) under argon atmosphere, diisopropylethylamine (0.14 mL, 0.86 mmol) was added. After stirring at room temperature for 5 min, a solution of D-erythro-sphingosine (114 mg, 0.38 mmol) in dichloromethane (3 mL) was added. The reaction mixture was stirred for 1.5 h. After dilution with dichloromethane (30 mL), the solution was washed with 1 M hydrochloric acid and dried over sodium sulfate. The solvent was removed under reduced pressure and the residue was subjected to chromatographic purification (silica gel, petrol ether/ethyl acetate/methanol 10:10:1) to give 109 mg (69%) of the product as a colourless solid.

$^1$H-NMR (300 MHz, CDCl$_3$): delta=0.88 (t, 3H), 1.26 (s, 20H), 1.36 (m, 2H), 2.05 (q, 2H), 2.70 (br s, 2H), 3.42 (s, 3H), 3.60 (m, 2H), 3.68 (m, 2H), 3.70 (m, 1H), 3.95 (m, 2H), 4.03 (s, 2H), 4.30 (m, 1H), 5.53 (dd, 1H), 5.79 (dt, 1H), 7.54 (d, 1H). MS (ESI): m/z=438 (M+Na).

Example 5

Synthesis of compound 10l: 3-Methylated D-erythro-sphingosine

Compound 10l was obtained by following reaction sequence.

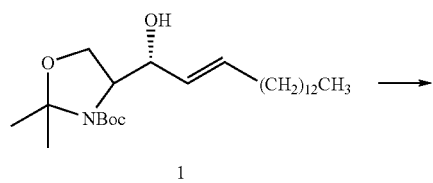

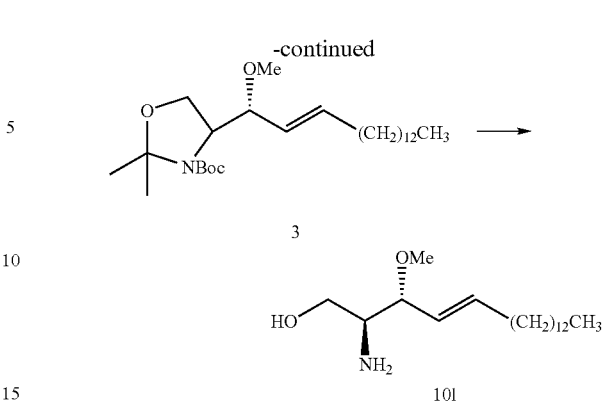

NaH (60%, 200 mg, 5 mmol) and MeI (0.34 mL, 5.5 mmol) were added subsequently to a solution of 1 (1.1 g, 2.5 mmol) in THF (10 mL), and the resulting reaction mixture was stirred at room temperature for 18 h. The reaction was quenched with H$_2$O (20 mL) and aqueous NaHCO$_3$ (20 mL) followed by extraction with Et$_2$O (2×50 mL). The combined organic layers were dried over sodium sulfate and concentrated in vacuo. Purification of the residue by flash chromatography (silica, PE/EtOAc 10:1) provided 2 as a colourless oil (720 mg, 63%).

$^1$H-NMR (300 MHz, CDCl$_3$): δ=0.85 (t, J=6.6 Hz, 3H), 1.25 (s, 20H), 1.46 (m, 14H), 2.05 (m, 2H), 3.26 (s, 3H), 3.39 (series of m, 4H), 5.29 (m, 1H), 5.61 (m, 1H).

1M HCl (4 mL) was added to a solution of 3 (950 mg, 2.09 mmol) in dioxane (8 mL) and heated at 95° C. for 2 h. The reaction was cooled to room temperature and quenched with saturated aqueous NaHCO$_3$ (100 mL) followed by extraction with Et$_2$O (2×150 mL). The combined organic layers were dried over sodium sulfate and concentrated in vacuo. Purification of the residue by flash chromatography (silica, CH$_2$Cl$_2$/MeOH 10:1) yielded 10l as a light yellow oil (650 mg, 99%).

$^1$H-NMR (300 MHz, CDCl$_3$): δ=0.85 (t, J=7.1 Hz, 3H), 1.20 (s, 20H), 1.28 (m, 2H), 2.05 (m, 2H), 2.51 (br s, 3H), 2.90 (m, 1H), 3.24 (s, 3H), 3.51 (m, 3H), 5.25 (m, 1H), 5.70 (m, 1H).

Example 6

Synthesis of Compound 10i

Acylation of compound 2 as described in the general procedure afforded compound 10i.

Yield: 94 mg; 58%.

$^1$H-NMR (300 MHz, CDCl$_3$): δ=0.86 (m, 3H), 0.95 (t, J=7.5 Hz, 3H), 1.26 (s, 24H), 1.32 (s, 6H), 1.64 (m, 1H), 2.02 (m, 2H), 2.21 (t, J=7.5 Hz, 1H), 2.79 (t, J=5.8 Hz, 2H), 3.68 (m, 1H), 3.89 (m, 1H), 4.30 (m, 1H), 5.27 (m, 6H), 5.54 (m, 1H), 5.74 (m, 1H), 6.26 (d, J=7.3 Hz, 1H). MS (ESI): m/z=560.4 (M+).

Example 7

Synthesis of Compound 10j

Acylation of compound 2 as described in the general procedure afforded compound 10j.

Yield: 180 mg; 67%.

$^1$H-NMR (300 MHz, CDCl$_3$): δ=0.86 (m, 3H), 1.26 (s, 46H), 1.59 (m, 4H), 2.02 (m, 3H), 2.21 (m, 2H), 3.68 (m, 1H), 3.72 (m, 2H), 4.02 (t, J=6.77 Hz, 2H), 4.32 (m, 1H), 5.54 (m, 1H), 5.74 (m, 1H), 6.28 (d, J=7.5 Hz, 1H).

Example 8

Synthesis of Compound 10k

Acylation of compound 10l as described in the general procedure afforded compound 10k.
Yield: 80 mg; 67%.
$^1$H-NMR (300 MHz, CDCl$_3$): δ=0.86 (m, 6H), 1.26 (s, 26H), 1.62 (m, 2H), 2.04 (m, 2H), 2.20 (m, 3H), 3.26 (s, 3H), 3.56 (m, 1H), 3.82 (m, 3H), 5.31 (m, 1H), 5.72 (m, 1H), 6.28 (d, J=7.6 Hz, 1H).

Example 9

Synthesis of Compound 10m

Acylation of compound 2 as described in the general procedure afforded compound 10m.
Yield: 65 mg; 53%.
$^1$H-NMR (300 MHz, CDCl$_3$): δ=0.86 (m, 3H), 1.26 (s, 43H), 1.57 (m, 4H), 2.04 (m, 3H), 2.21 (m, 2H), 2.35 (br s, 1H), 3.62 (m, 3H), 3.66 (m, 2H), 4.32 (m, 1H), 5.55 (m, 1H), 5.76 (m, 1H), 6.27 (d, J=7.5 Hz, 1H).

Example 10

Synthesis of Compound 10n

Compound 10n was obtained by the following reaction sequence.

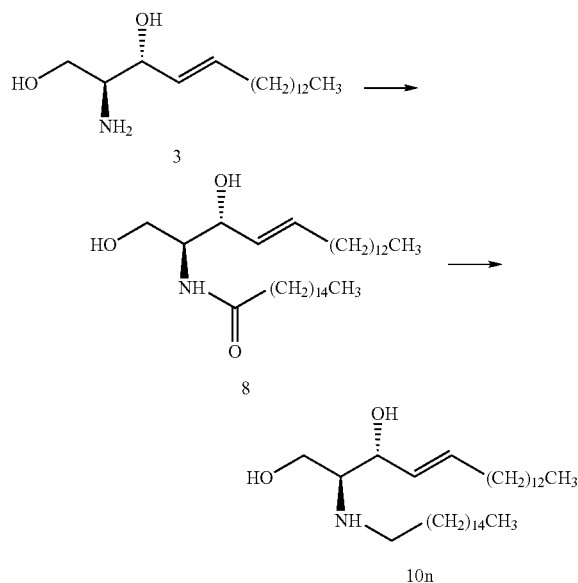

Acylation of compound 2 as described in the general procedure afforded compound 8.
Yield: 62 mg; 41%.
$^1$H-NMR (300 MHz, CDCl$_3$): δ=0.86 (m, 6H), 1.26 (m, 42H), 1.63 (m, 3H), 2.05 (m, 6H), 2.21 (m, 2H), 3.70 (m, 1H), 3.94 (m, 2H), 4.31 (m, 1H), 5.55 (m, 1H), 5.76 (m, 1H), 6.24 (m, 1H).
A solution of 8 (146 mg, 0.27 mmol) in dry THF (20 mL) was added dropwise to a solution of LiAlH$_4$ (1M solution in THF) (2.0 mL, 2.0 mmol). The mixture was heated at reflux for 16 h, quenched with water (100 mL) and extracted with EtOAc (3×100 mL). The combined organic layers were dried over sodium sulfate and concentrated in vacuo. Purification of the residue by flash chromatography (silica, CH$_2$Cl$_2$/MeOH 10:1) yielded 10n as a white solid (49 mg, 34%).
$^1$H-NMR (300 MHz, CDCl$_3$): δ=0.86 (m, 6H), 1.26 (s, 42H), 1.83 (m, 3H), 2.05 (m, 4H), 2.92 (m, 2H), 3.02 (m, 4H), 3.92 (m, 1H), 4.03 (m, 1H), 4.70 (m, 2H), 5.42 (m, 1H), 5.75 (m, 1H). MS (ESI): m/z=524.5 (M+1).

Example 11

Synthesis of Compound 10o

Compound 10o was obtained by the following reaction sequence.

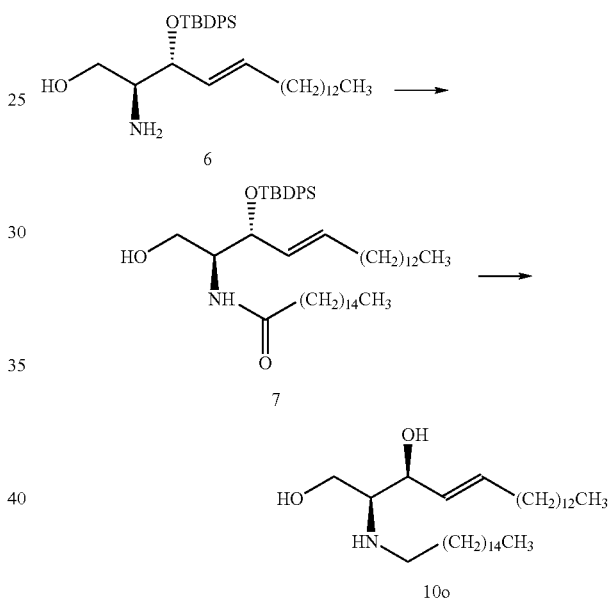

Acylation of compound 6 as described in the general procedure afforded compound 7.
Yield: 1.685 g, 87%.
$^1$H-NMR (300 MHz, CDCl$_3$): δ=0.84 (m, 6H), 1.04 (s, 6H), 1.24 (m, 44H), 1.49 (m, 4H), 1.86-2.33 (m, 6H), 2.79-2.95 (m, 2H), 3.58 (m, 1H), 3.85 (m, 2H), 4.32 (m, 1H), 5.38 (m, 2H), 5.92 (m, 1H), 7.35 (m, 6H), 7.59 (m, 4H). MS (ESI): m/z=776 (M+1).
A solution of 7 (217 mg, 0.28 mmol) in dry THF (15 mL) was cooled to 0° C. and a solution of LiAlH$_4$ (1M solution in THF) (0.842 mL, 0.84 mmol) was added dropwise. The mixture was stirred at 0° C. for 2 h and at room temperature for 16 h. The reaction was quenched with water (100 mL) and extracted with CH$_2$Cl$_2$ (3×100 mL). The combined organic layers were dried over sodium sulfate and concentrated in vacuo. Purification of the residue by flash chromatography (silica, EtOAc) yielded 10o as a white solid (83 mg, 57%).
$^1$H-NMR (300 MHz, CDCl$_3$): δ=0.86 (m, 6H), 1.26 (s, 46H), 1.52 (m, 5H), 2.05 (m, 2H), 2.43 (m, 2H), 2.70 (m, 2H), 3.42 (m, 1H), 3.73 (br s, 2H), 4.21 (m, 1H), 5.42 (m, 1H), 5.75 (m, 1H). MS (ESI): m/z=524.6 (M+1).

Example 12

Synthesis of Compound 10p

Acylation of compound 2 with farnesoic acid as described in the general procedure afforded compound 10p.

Yield: 426 mg; 82%.

$^1$H-NMR (300 MHz, CDCl$_3$): δ=0.86 (m, 6H), 1.25 (m, 18H), 1.34 (m, 2H), 1.60 (s, 6H), 1.68 (s, 3H), 1.95 (m, 9H), 2.21 (m, 2H), 2.34 (br s, 1H), 2.63 (m, 1H), 3.70 (m, 1H), 3.94 (m, 2H), 4.34 (m, 1H), 5.06 (m, 2H), 5.51 (m, 1H), 5.61 (br s, 1H), 5.75 (m, 1H), 6.20 (d, J=6.9 Hz, 1H). MS (ESI): m/z=518 (M+1).

Example 13

Synthesis of Compound 10q

Acylation of compound 10l with farnesoic acid as described in the general procedure afforded compound 10q.

Yield: 50 mg; 25%.

$^1$H-NMR (300 MHz, CDCl$_3$): δ=0.84 (m, 3H), 1.24 (m, 20H), 1.34 (m, 2H), 1.59 (s, 6H), 1.67 (s, 3H), 1.97 (m, 13H), 3.25 (s, 3H), 3.58 (m, 1H), 3.85 (m, 3H), 5.05 (m, 2H), 5.32 (m, 1H), 5.60 (br s, 1H), 5.68 (m, 1H), 6.21 (d, J=7.7 Hz, 1H). MS (ESI): m/z=518 (M+1).

Example 14

Synthesis of Compound 10r

Acylation of compound 2 with farnesoic acid as described in the general procedure afforded compound 10r.

Yield: 345 mg; 88%.

$^1$H-NMR (300 MHz, CDCl$_3$): δ=0.85 (m, 6H), 1.25 (m, 22H), 1.29 (m, 2H), 1.70 (m, 2H), 2.01 (m, 8H), 2.21 (t, J=7.6 Hz, 2H), 2.79 (m, 12H), 3.68 (m, 1H), 3.90 (m, 2H), 4.32 (m, 1H), 5.34 (m, 8H), 5.48 (m, 1H), 5.74 (m, 1H), 6.25 (d, J=6.9 Hz, 1H).

Example 15

Synthesis of Compound 10s

Acylation of compound 10l as described in the general procedure afforded compound 10s.

Yield: 100 mg; 26%.

$^1$H-NMR (300 MHz, CDCl$_3$): δ=0.85 (m, 6H), 1.25 (m, 22H), 1.29 (m, 2H), 1.69 (m, 2H), 2.04 (m, 8H), 2.21 (t, J=7.6 Hz, 2H), 2.80 (m, 8H), 3.25 (s, 3H), 3.56 (m, 1H), 3.83 (m, 3H), 5.30 (m, 9H), 5.74 (m, 1H), 6.25 (d, J=6.9 Hz, 1H).

Example 16

Synthesis of Compound 10u

Acylation of compound 2 as described in the general procedure afforded compound 10u.

Yield: 67 mg; 45%.

$^1$H-NMR (300 MHz, CDCl$_3$): δ=0.86 (m, 3H), 1.26 (m, 20H), 1.34 (m, 2H), 2.02 (m, 2H), 3.41 (s, 3H), 3.71 (m, 1H), 3.90 (m, 4H), 4.32 (m, 1H), 5.49 (m, 1H), 5.75 (m, 1H), 7.21 (d, J=7.4 Hz, 1H).

Example 17

Synthesis of Compound 10v

Acylation of compound 10l as described in the general procedure afforded compound 10v.

Yield: 70 mg; 43%.

$^1$H-NMR (300 MHz, CDCl$_3$): δ=0.86 (m, 3H), 1.26 (m, 20H), 1.35 (m, 2H), 2.03 (m, 2H), 3.27 (s, 3H), 3.38 (s, 3H), 3.53 (m, 1H), 3.63 (m, 16H), 3.78 (m, 1H), 3.89 (m, 2H), 4.00 (m, 2H), 5.31 (m, 1H), 5.70 (m, 1H), 7.34 (d, J=8.3 Hz, 1H).

Examples 18 and 19

Synthesis of Compounds 10w and 10x

Compounds 10w and 10x were obtained by the following reaction sequence.

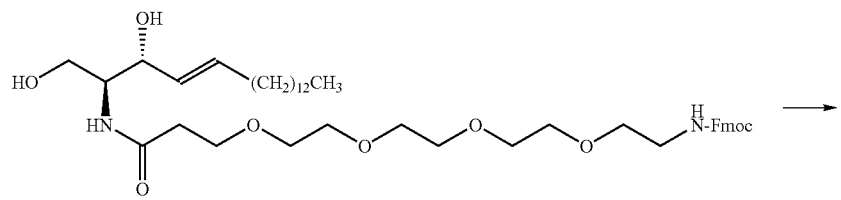

13

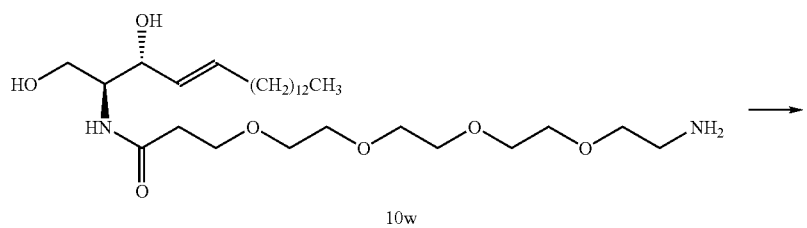

10w

-continued

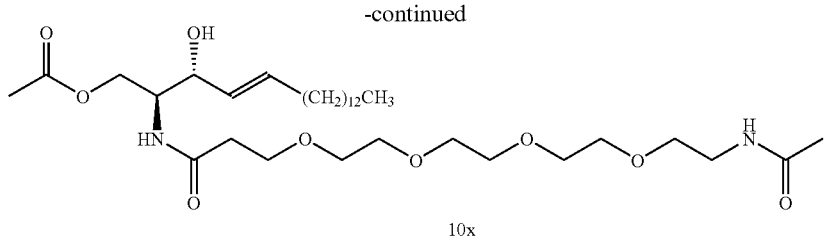

10x

Acylation of compound 2 as described in the general procedure afforded compound 13. The crude material was subjected to the next transformation.

Yield: 188 mg; 64%.

To a solution of 13 (178 mg, 234 mmol) in $CH_2Cl_2$ (10 mL) was added piperidine (231 μL, 2.34 mol) and the resulting mixture was stirred at room temperature for 30 min. The solvent was removed under reduced pressure and purification of the residue by flash chromatography (silica, $CH_2Cl_2$/MeOH 10:1) yielded 10w as a white solid (105 mg, 82%).

$^1$H-NMR (300 MHz, $CDCl_3$): δ=0.86 (m, 3H), 1.26 (m, 20H), 1.47 (m, 2H), 2.03 (m, 2H), 2.52 (m, 1H), 2.64 (m, 1H), 3.15 (m, 1H), 3.62 (m, 20H), 4.28 (m, 1H), 5.55 (m, 1H), 5.76 (m, 1H), 8.21 (d, J=7.5 Hz, 1H).

Acylation of compound 10w with acetic acid as described in the general procedure afforded compound 10x.

Yield: 10 mg; 10%.

$^1$H-NMR (300 MHz, $CDCl_3$): δ=0.86 (m, 3H), 1.24 (m, 20H), 1.27 (m, 2H), 1.98 (m, 6H), 2.46 (m, 2H), 3.42 (m, 2H), 3.53 (m, 2H), 3.60 (m, 16H), 4.22 (m, 4H), 5.45 (m, 1H), 5.72 (m, 1H), 6.52 (br s, 1H), 6.84 (d, J=6.9 Hz, 1H). MS (ESI): m/z=553.3 (M+Na).

Example 20

Disrafter Assay, Disrafter-Liposome Raftophile Assay (D-LRA)

In accordance with the present invention, the disrafting capacity of a given compound and its medical usefulness in the amelioration, treatment or prevention of a disease related to lipid raft processes may be tested by a D-LRA provided herein.

The raftophilicity of certain fluorescent indicators varies with the raft content of liposomes which, in turn, is determined by their lipid composition and the presence of raft modulators.

The D-LRA assay detects two extremes of raft modulation, disrafting and raft augmentation. % disrafting below 0 results from an actual increase in partition of the indicator, caused by an increased raft content of the liposomes. This can result from a restructuring of the rafts, i.e. an increased density, or physical insertion of the test compounds into the liposomes increasing raft quantity. Significance can be ascribed to values above 25% (disrafting) and below −25% (disrafters by "augmentation").

Liposomes (defined below) with a raft content of about 50% are incubated with potential disrafters. The change in raft content is then determined with an indicator (standard raftophile).

Material for D-LRA

1. Liposomes

Raft liposomes: (35% cholesterol, 10.5% shingomyelin (SM), 3.5% GM1, 25.5% phosphatidylethanolamine (PE) and 25.5% phosphatidylcholine (PC))

Non-raft liposomes: N liposomes (50% PE, PC)

Liposomes are prepared by spreading lipids dissolved in tert. butanol on a glass surface at 50° C. in a rotary evaporator rinsed with nitrogen. After 6 h desiccation the lipids are taken up in 40 mM octyl-β-D-glucoside (OG) to a concentration of 1 mg/ml and dialysed for 24 h against 2 changes of 5 l PBS with 25 g Biobeads (Amberlite XAD-2) at 22° C.

2. Indicators

Indicators are fluorescent compounds which preferentially partition into rafts. These are selected to represent different structural classes, and different excitation/emission wavelengths. This is important when raft modulators are tested which interfere with indicator fluorescence.

2.1. Perylene is a raftophilic compound which embeds completely into membranes.

2.2. GS-96 is a raftophilic adduct of the general structure cholesterol-linker-rhodamine-peptide (only the cholesterol is membrane-inserted). The structure of GS-96 is Cholesteryl-Glc-RR-βA-D(Rho)-βA-GDVN-Sta-VAEF (one-letter amino acid code; Glc=glycolic acid, βA=β-alanine, Rho=rhodamine, Sta=statine; Fmoc-Statine Neosystem FA08901, Strasbourg, France) and was generated by applicant using standard procedures: peptide synthesis was carried out on solid support using the 9-fluorenylmethyloxycarbonyl (Fmoc) method with piperidine as deprotecting reagent and 2-(1H-benzotriazol-1-yl)-1,1,3,3-tetramethyluronium hexafluorophosphate (HBTU) as coupling reagent employing an Applied Biosystems 433A peptide synthesizer. Fmoc-protected amino acid building blocks are commercially available, except of rhodamine-labelled Fmoc-glutamic acid, which was prepared by a modified procedure extracted from literature (T. Nguyen, M. B. Francis, Org. Lett. 2003, 5, 3245-3248) using commercially available Fmoc-glutamic acid tert-butyl ester as substrate. Final saponification generated the free acid used in peptide synthesis. Cholesteryl glycolic acid was prepared as described in literature (S. L. Hussey, E. He, B. R. Peterson, Org. Lett. 2002, 4, 415-418) and coupled manually to the amino function of the N-terminal arginine. Final cleavage from solid support using standard procedures known in peptide synthesis and subsequent purification by preparative HPLC afforded GS-96.

2.3. J-12S is a smaller adduct serving the same purpose: Cholesteryl-Glc-RR-βA-D(Rho). Other indicators, e.g. sphingomyelin adducts, are equally suitable.

Sketched Method of D-LRA

Liposomes are diluted into PBS to a final lipid concentration of 200 μg/ml (R: 302 μM, N: 257 μM total lipid)

Preincubate 100 µl liposomes 30 min 37° C. on a thermomixer (1000 rpm)
Add 1 µl test compound stock solution (100 µM final concentration) or appropriate solvent controls and incubate 2 h as above
Add indicator (GS-96 0.2 µM or perylene 2 µM) and incubate a further 1 h
Proceed as for LRA: centrifuge 20 min in the TLA-100 rotor of the Beckman Optima centrifuge at 400 000 g and 37° C.
Withdraw the top 50 µl of the supernatant (S) and transfer to a microtiter plate containing 150 µl 50.3 mM OG
From tubes incubated in parallel transfer the total liposomes (L) to microtiter wells containing 100 µl 80 mM OG
Wash the tubes with 200 µl 40 mM OG (GS-96) or 100 mM C8E12 (perylene) at 50° C. on the thermomixer (1400 rpm) to elute adherent (A) indicator and transfer content to microtiter plate
Prepare 200 µl indicator concentration standards in 40 mM in the microtiter plate
Determine the indicator concentrations in S, L and A in a fluorimeter/plate reader (Tecan Safire)
Compute partition coefficients CpN, CpR and raftophilicity ($r\Phi$=CpR/CpN) with respect to CpN
Calculate disrafting activity as % disrafting=$100*(r\Phi_{control}-r\Phi_{test\ compound})/r\Phi_{control}$ Detailed Method N and R Liposomes were diluted into PBS to a final lipid concentration of 200 µg/ml and 100 µl aliquots preincubated 30 min 37° C. on a thermomixer (1000 rpm).

1 µl of DMSO (solvent controls) and the test compound stock solutions (all 10 mM in DMSO, except where noted) were added and incubated 2 h as above.

1 µl indicator in DMSO was then added (final indicator concentrations GS-96 0.2 µM, perylene 2 µM) and incubation continued for 1 h as above Incubation mixes were centrifuged 20 min in the TLA-100 rotor of the Beckman Optima centrifuge at 400 000 g (37° C.). 50 µl of the supernatant (S) was transferred from the top of the tube to a 96-well microtiter plate containing 150 µl 50.3 mM OG in PBS.

From tubes incubated in parallel the total liposomes (L) were transferred to microtiter wells containing 100 µl 80 mM OG in PBS. The tubes was then washed with 200 µl 40 mM OG (GS-96) or 100 mM C8E12 (perylene) at 50° C. on the thermomixer (1400 rpm) to elute adherent (A) indicator and content transferred to the microtiter plate.

200 µl indicator concentration standards were prepared in 40 mM OG in the microtiter plate.

The 96-well plate was read in a fluorimeter/plate reader (Tecan Safire) at the appropriate wavelengths, excitation 411 nm, emission 442 nm (perylene); excitation 553 nm, emission 592 nm (GS-96). Based on the concentration standards fluorescence readings were converted to indicator concentrations.

From the concentration data partition coefficients CpN and CpR were computed as follows:

The indicator concentrations in the respective phases are denoted L (in total liposomes), A (adherent to the tube wall), S (in the aqueous phase).

Cp=f*(L−S)/S. f*(L−S) is the compound concentration in the membrane, where f is the ratio of incubation volume to actual lipid bilayer volume.

The raftophilicity was calculated as the ration of the two partition coefficients, $r\Phi$=CpR/CpN.

Disrafting activity was calculated as follows:

% disrafting=$100*(r\Phi_{control}-r\Phi_{test\ compound})/r\Phi_{control}$.

Results: In the following table the disrafting activities of preferred compounds are provided using perylene as marker as outlined above, except in the case of 10p, where GS-96 was employed as marker. All test compounds were submitted to the DLRA at concentrations of 100 µM.

| Compound | Disrafting Activity [%] |
|---|---|
| 10a | 99.2 |
| 10b | 80.5 |
| 10c | 94.2 |
| 10d | 85.9 |
| 10e | 54.8 |
| 10f | 58.6 |
| 10g | 89.3 |
| 10h | 72.2 |
| 10i | 70.4 |
| 10j | 58.8 |
| 10k | 98.6 |
| 10n | 94.8 |
| 10o | 91.0 |
| 10p | 58.9 |
| 10r | 32.7 |
| 10u | 97.0 |
| 10v | 96.1 |
| 10w | 53.1 |
| 10x | 65.5 |

All compounds tested in the DLRA assay provided medium to high positive values and can be considered to be disrafters in the context of the present invention and may suitably be employed in pharmaceutical compositions. As indicated by the positive values obtained in the DLRA assay, all compounds exert raft modulation by disrafting according to the above given definition.

Example 21

Virus Budding Assay (Influenza Assay)

The aim of this assay is the identification of compounds targeting raft-dependent virus budding and to distinguish from inhibitor effects on other stages of virus reproduction.

Principle of Virus Budding Assay

Nascent virus (influenza) on the cell surface is pulse-biotinylated 6 or 13 h post infection and treated with test compounds for 1 h. Biotinylated virus is captured on a streptavidin-coated microtiter plate. Captured virus is detected with virus-specific primary and peroxidase-labeled secondary antibody. A luminescent signal generated from a peroxidase substrate is recorded with a CCD camera (LAS 3000). Intensities are evaluated by densitometry.

Value less than 100% reveal inhibition of virus budding. Significance can be ascribed to values below 80%, preferably below 70%. Values above 100% mean that more viruses are released than in the untreated control. This reflects a change in regulation of virus release which can have various causes. In this case significance can be ascribed to values above 130%. These will be followed up if the compound is inhibitory in an assay of virus replication.

Materials of Virus Budding Assay

1. Infection 96-well plate MDCK 1-2 d

Influenza virus stocks

IM (infection medium): MEM+Earle's (Gibco/InVitrogen 21090-022) plus 2 mM L-glutamin, 10 mM Hepes, bovine serum albumin (BSA) 0.2%

2. Biotin Labelling stock solutions: 20% glucose (about 1 M), 1 M glycin
PBS8G: PBS pH 8, 1 mM glucose, ice-cold
biotin, 20 μg-100 μl-per well of 96-well plate, 1 mg biotin/5 ml PBS8G freshly prepared on ice
Quench medium (1M, 10 mM glycine), ice cold 3. Chase and Harvest Aluminum thermoblocks for plate T shift and test compound dilutions
IM +/− test compounds, 37° C.
TBS (Tris-buffered saline pH 7.4, 10 mM Tris, 150 mM NaCl); TBS$^{+++}$=TBS plus protease inhibitors: dilute 5% trypsin inhibitor 1:250, 200 mM AEBSF 1:200 and 1 mg/ml aprotinin 1:100.
ice-cold 96-well plates (v-bottom) and MP3300 multiwell plate rotor of the Multifuge 1-S-R (Heraeus) centrifuge 2° C.

4. Capture streptavidin-coated 96-well plate Reacti-Bind™ Streptavidin HBC (Pierce 15500)

Sketched Method of Virus Budding Assay

1. Infection and Neuraminidase Treatment wash wells with 2×200 μl IM. Infect with 100 μl virus diluted in IM at a multiplicity of infection 0.5-2 infectious units per cell for 30 min at 37° C. Remove inoculum and replace by 150 μl IM.
incubate for 6 or 13 h post-infection (p.i.)

2. Biotinylation place plate on ice, wash 4×0.20 ml ice-cold PBS8G
add 0.1 biotinylation solution in PBS8G per well
rock 12 min on ice in refrigerator
wash 5× with 0.25 ml quench medium on ice 3. Budding/Chase transfer plate to preheated aluminum block
exchange last wash for 125 μl pre-warmed medium +/− test compounds (i.e. compounds to be tested and considered as "disrafters", "disrafting compounds in D-LRA described above)
return plate on block to incubator for 1 h 37° C.

4. Harvest place on ice
transfer 50 μl overlays to v-bottom centrifugation plate containing 50 μl TBS+++ on ice (1:1 dilution)
centrifuge the plate 30 min 2° C. 4400 rpm
alternative equivalent protocol: transfer overlays to Millipore (MSDVS6510) clear filtration plates MS HTS™ DV, 0.65 μm hydrophilic low protein binding and centrifuge 1 min, 1500 g, into a Nunc assay plate.

5. Capture prepare streptavidin-coated plate by washing with 3×200 μl TBS/0.1% Tween and once with TBS
transfer 50 μl virus overlay supernatants to capture plate
capture on rocker 2 h at 37° C. or over-night at 4° C.

6. Detection to capture plate add 50 μl TBS, 40 mM OG and incubate on a rocker for 20 min at 4° C.
wash capture plate 1× with 200 μl TBS
add 200 μl block and incubate 2 h at room temperature or over-night at 4° C.
develop with antiNP monoclonal (MAb pool 5, US Biological 17650-04A) diluted 1:1000 in block, 1 h at room temperature and wash 3×
use rabbit anti-mouse-peroxidase conjugate 1:2000 as secondary antibody, 1 h at room temperature and wash 3×
develop with Pierce Super Signal (West-Dura) luminescent, or fluorescent or colorimetric substrate
image with CCD camera (LAS 3000, Raytest) and quantify densitometrically Results: It is exemplified that particularly good results were obtained in the virus budding assay with 10b ($C_2$ dihydroceramide), 10d (N-oleoyl-D-sphingosine) and 10h (N-(3, 6-oxa-heptanoyl)-D-erythro-sphingosine). These compounds are therefore suitable compounds for the development of pharmaceutical compositions used for the treatment of influenza infection. Nevertheless, effects observed in the influenza virus reproduction and infectivity assay (cf. the following example) are further experimental results to be used to demonstrate the usefulness of the compounds provided in the present invention in a medical setting.

Example 22

Virus Reproduction and Infectivity Assay (Focus Reduction Assay)

The aim of this assay is identifying disrafting compounds inhibiting virus replication or lowering virus infectivity.

Principle

Assay of antiviral effects under conditions of virus titration, equivalent to a traditional plaque reduction assay, except that it is done on microtiter plates and developed as a cell Elisa. Cells are briefly preincubated with test compound dilutions and then infected with serially diluted virus.

Materials

Low retention tubes and glass dilution plate ((Zinsser) from 70% EtOH, dried under hood)
2 Thermomixers, 1.5 ml Eppendorf and 96-well blocks
96-well plates MDCK cells 1-2 d
Virus aliquots with known titer
IM (infection medium)
trypsin 1 or 2 mg/ml stock solution, freshly prepared.
glutaraldehyde (Sigma, ampoules, kept at −20° C.)
0.05% in PBS (dilute 1:500), freshly prepared, 250 ml per plate
Antibodies for cell Elisa development; Pierce SuperSignal (West Dura) substrate Method 1. Compound Dilutions Thaw out test compounds at 37° C. and sonicate if necessary
Preheat IM in low retention tubes at 37° C. in a thermomixer and add test compounds [μl] as follows:
100 μM: 1078+22 μl
50 μM: 1089+11 μl
25 μM: 1094.5+5.5 μl
10 μM: 1098+2.2
After at least 30 min shaking compound dilutions are transferred into a glass 96-well plate preheated in a thermomixer microplate block at 37° C.
For two titration plates one glass plate is sufficient, the left half receives the test media for plate 1, the right half for plate 2. Each well receives 250 μl test medium (see template below)

2. Infection

Predilute virus 1:64 in IM (630 μl+10 μl). Dilute virus in cold IM 1:2000 (=1) and then make 2 further two-fold dilutions. For one 96-well plate prepare 3, 1.5, 1.5 ml, for two plates 6, 3, 3 ml and keep at 4° C.

Weigh out trypsin, prepare a solution 20 µg/ml and put through a 0.2 µm sterile syringe filter. Then dilute to 4 µg/ml in IM.

Shortly before infection add 1 vol. trypsin (4 µg/ml) to virus dilutions or to IM (for mock infection) and keep at 4° C. until infection.

Wash monolayers 2×200 µl IM.

With a multichannel pipette add 100 µl test compounds or solvent controls in 1M, so that each column (2 to 11) contains one test compound dilution. (1 and 12 receive IM and can serve as additional controls if edge effects are minimal.)

With a multichannel pipette add 100 µl 1M, 2 µg trypsin/ml to rows A and H (mock infection). Add virus dilutions to the other rows, changing tips every time. After each addition pipet up and down.

Incubate 16 h at 37° C.

Microscopy: Assess toxicity/cell morphology/precipitation in mock-infected wells.

Terminate infection by fixing and immersing/filling the whole plate with 250 ml 0.05% glutaraldehyde for at least 20 min RT.

3. Detection

Shake off the glutaraldehyde and rinse with PBS.

Permeabilize 30 min with 50 µl 0.1% TX-100 in PBS and rinse with PBS.

Block 1 h on a rocker at RT or over-night at 4° C. in TBS/Tween/10% FCS.

Develop with anti-NP (MAb pool 5) diluted 1:1000 in block, 1 h RT and wash 3× with TBS/Tween.

Add peroxidase conjugated secondary anti-mouse antibody at about 1:2000, 1 h on a rocker at RT and wash 2×TBS/Tween, once with TBS.

4. Imaging develop with SuperSignal West Dura (Pierce 34076).

image with CCD camera LAS 3000 (Fuji/Raytest) at high resolution: use Fresnel lense.

quantify by densitometry using mock-infected controls as background.

Quantification of Assay Results

The edge columns of a 96-well plate with MDCK cell monolayers are non-infected but treated with test compound and serve as background controls (well a) for densitometric evaluation (see below). Three further wells b, c and d are infected with virus dilutions, e.g. 1:512 000, 1:256 000 and 1:128 000, so that the 1:128 000 dilution will generate 50 to 100 foci. Suitable dilutions were determined by virus titration.

Foci of infected cells are developed immunohistochemically. Initially all wells are blocked for 1 h or over night on a rocker with 200 µL per well of a mixture of PBS+10% heat-inactivated fetal calf serum (block). This is followed by 1 h with 50 µL per well antibody to viral nucleoprotein (MAb pool 5, US Biological I 7650-04A) 1:1000 diluted in block. Antibody is removed by three times 5 min washes with TBS (Tris-buffered saline)/Tween (0.1%) (TT). The next incubation is 1 h with 50 µL per well rabbit-anti-mouse-HRP (coupled to horseradish peroxidase) 1:2000 diluted in block. Finally, two washes as above and one with TBS.

The last wash is removed quantitatively and replaced by 50 µL per well substrate (Pierce 34076). The plate is exposed 5 to 10 min through the pre-focused Fresnel lense of the LAS 3000 CCD camera (high resolution mode). Images are evaluated densitometrically. Initially the background is subtracted (well a, see above). The densitometric intensity is calculated as follows:

$$I = [0.25 \times i(\text{well } b) + 0.5 \times i(\text{well } c) + i(\text{well } d)]/1.75$$

wherein i is defined as 10000 times the intensity per area measured for the relevant well b, c or d. This calculation corresponds to the classical plaque assay. The factors represent the weighting of the individual values.

Results are expressed as % inhibition defined as follows:

% inhibition=100−% control wherein % control is calculated by multiplying a given I for test compound by 100 and dividing by I for the appropriate solvent control. If I is a control or solvent control, its value is set as 100%.

Results: Two of the compounds that both tested positive in the above-mentioned DLRA and were identified as disrafters, namely compounds 10e and 10f, were evaluated in the PR8 virus replication assay. They both provided good results. 10e inhibited virus replication by 21% at a concentration of 10 µM, while 10f inhibited the same process by 17% at 10 µM concentration. Thus, both substances are preferred compounds for the pharmaceutical intervention in influenza infection. Eight further compounds which tested positive in the DLRA, i.e. compounds 10i, 10k, 10n, 10o, 10p, 10q, 10r and 10w, provided for particular good results in the influenza virus replication assay and are thus even more preferred compounds to be used in the pharmaceutical compositions described herein for the treatment of influenza infection. In the case of compound 10i PR8 virus replication was inhibited by 48.9% at a concentration of 50 µM compared to solvent vehicle alone. Similarly, compound 10k inhibited the same process by 59.3% (at 20 µM concentration), compound 10n by 34.7% (at 100 µM), compound 10o by 40.8% (at 100 µM), compound 10p by 39.2% (at 100 µM), compound 10q by 61.6% (at 100 µM), compound 10r by 38% (at 100 µM) and compound 10w by 50.3% (at 25 µM). When using compound 10b at a concentration of 50 µM the virus replication was inhibited by 74%, thus making compound 10b an even more preferred compound for the treatment of influenza infection. In addition, also compounds 10g, 10h, 10j, 10u and 10v provided for particular good inhibitory activities in the PR8 influenza assay. Compound 10g inhibited virus replication by 70% when used in a concentration of 20 µM, while compound 10h inhibited by 75% at the same concentration, compound 10j by 44.6% (at 50 µM), compound 10u by 70.3% (at 20 µM) and compound 10v by 87.4% (at 20 µM). Consequently, these substances are even more preferred embodiments for use as therapeutics against influenza infection.

Example 23

Degranulation Assay

Mast cells are a widely used model system for hyperallergic reactions or asthma. On their surface they express high affinity receptors for IgE (FcεRI). Upon binding of antigen-specific IgE to the receptor cells become sensitive to antigen (allergen). When sensitized cells encounter multivalent antigen the clustering of IgE-FcεRI complexes initiates a cascade of cellular events that ultimately leads to degranulation, that is release of mediators of inflammation and cellular activation, such as cytokines, eicosanoids, histamine and enzymes. Several steps in this cascade are raft-dependent, such as antigen-triggered relocation of FcεRI to rafts, disruption of the signaling complex assembled around LAT and/or dislocation of phosphoinositides, $Ca^{2+}$-influx (raft localization of plasma membrane calcium channels), membrane ruffling (cytoskeletal reorganizations involving Akt/WASP/FAK) and exocytosis. Therefore, the assay can be used as a screening method to identify raft-modulating compounds, in particular compounds useful in the medical management of asthma. Especially in conjunction with other assays for pre-selection of raft-modulating compounds the assay is a powerful tool to demonstrate the effectiveness of such compounds for intervention in biological processes.

1. Introduction

The assay measures release of β-hexosaminidase as a marker of release of various preformed pharmacological agents in response to clustering of the high affinity IgE receptor (FcεRI) by means of multivalent antigen-IgE complexes. Rat basophilic leukemia (RBL-2H3) cells, a commonly used model of mast cell degranulation, are sensitized with anti-DNP specific IgE and challenged with multivalent DNP-BSA. The release of β-hexosaminidase into the supernatant is measured by enzymatic conversion of the fluorogenic substrate 4-methylumbelliferyl-N-acetyl-β-D-glucosaminide to N-acetyl-β-D-glucosamine and highly fluorescent methylumbelliferone and quantified by fluorescence detection in a Tecan Safire T plate reader.

2. Materials

Chemicals and Specialty Reagents

Surfact-Amps X-100 solution was obtained from Pierce, DNP-bovine albumin conjugate (DNP-BSA) and 4-methylumbelliferyl-N-acetyl-β-D-glucosaminide (MUG) were from Calbiochem, tri(ethylene glycol) monoethyl ether (TEGME) from Aldrich, DMSO Hybri-Max and human DNP-albumin from Sigma. Rat anti-DNP IgE monoclonal antibody was acquired from Biozol. All cell culture media, buffers and supplements were obtained from Invitrogen except fetal calf serum (FCS) which was from PAA Laboratories (Cölbe, Germany). Other reagents were of standard laboratory quality or better.

Other chemicals are standard laboratory grade or better if not specified otherwise.

Buffers and Solutions

Phosphate buffered saline (PBS) and 1 M HEPES were provided by the in-house service facility. Tyrode's buffer (TyB) consisted of Minimum Essential Medium without Phenol Red (Invitrogen) supplemented with 2 mM GlutaMAX™-I Supplement (Invitrogen) and 10 mM HEPES. Lysis buffer consisted of 25 mM Tris-HCl, pH 7.5, 150 mM NaCl, 5 mM EDTA and 1% (w/v) Triton X-100. Human DNP-BSA was dissolved to 1 mg/ml in Millipore water. MUG substrate solution was 2.5 mM 4-methylumbelliferyl-N-acetyl-β-D-glucosaminide 0.05 M citrate, pH 4.5 and stop solution was 0.1 M NaHCO$_3$/0.1 M Na$_2$CO$_3$, pH 10.

Cell Culture

RBL-2H3 cells obtained from the German Collection of Microorganisms and Cell Cultures (Braunschweig, Germany) were maintained in 70% Minimum Essential Medium with Earle's Salts/20% RPMI 1640/10% heat-inactivated fetal calf serum) supplemented with 2 mM GlutaMAX™–I in 5% CO$_2$ at 37° C. and routinely checked to be free of mycoplasma contamination. Cells grown in 175 cm$^2$ flasks were split with 0.05% Trypsin/EDTA and resuspended in 20 ml fresh medium. One hundred and 50 µl cell suspension were plated per well into 24 well cluster plates (Costar, Schiphol-Rijk, Netherlands) and cells were used one or two days after plating, respectively.

3. Measurement of β-Hexosaminidase Release

Method

Two to 24 hours before incubation with test compounds medium was removed and cells were sensitized with 0.4 µg/ml anti-DNP IgE in fresh medium. Following sensitization, cells were washed once with warm TyB and incubated for 60 min with test compound at a maximum of 100 µM or the highest non-toxic concentration (total vehicle concentration adjusted to 1%) or 1% vehicle in TyB at 37° C. DNP-HSA (0.1 µg/ml final concentration) or buffer alone was added and cells incubated for 15 min at 37° C. Plates were centrifuged at 4° C. for 5 min at 250×g and immediately transferred to ice. Supernatants were collected and the cells lysed with lysis buffer. Hexosaminidase activity in supernatants and lysates was measured by incubating 25 µl aliquots with 100 µl MUG substrate solution in a 96-well plate at 37° C. for 30 min. The reaction was terminated by addition of 150 µl stop solution. Fluorescence was measured in a Tecan Safire™ plate reader at 365 nm excitation and 440 nm emission settings.

Quantification of Assay Results

Each compound is tested in duplicates in at least three independent experiments. β-hexosaminidase release is calculated after subtraction of unspecific release (release without addition of antigen) using the formula:

% degranulation=100×$RFU$ supernatant/$RFU$ lysate

Inhibition of β-hexosaminidase release with respect to control is calculated as follows:

% inhibition=100×(1−($RFU$ supernatant of compound/$RFU$ supernatant of control))

Values for CTB internalization from independent experiments are averaged and accepted when the standard deviation (SD)≦15%.

Results: All compounds which tested positive in the DLRA assay were further scrutinized in the degranulation assay. Particularly good results were obtained with compounds 10g, 10h and 10u, which thus represents preferred compounds to be used in the pharmaceutical compositions described herein for the treatment of asthma and related immunological diseases. Compound 10g inhibited the release of β-hexosaminidase by 65% at a concentration of 25 µM compared to solvent vehicle alone. Similarly, compound 10h inhibited the same process by 71% (at 25 µM) and compound 10u by 63% (at 25 µM). Even better results were obtained when evaluating compound 10c, which inhibited the same process by 94% (at 100 µM), compound 10l, which inhibited by 84% (at 25 µM), and compound 10v, which inhibited by 74% (at 12.5 µM). Remarkably, the most preferred embodiment for the treatment of asthma and related immunological diseases is compound 10w, which inhibited by 69% (at 6.25 µM).

Example 24

Simian Virus 40 (SV40) Assay

Uptake of Simian Virus 40 (SV40) is a model for infection by diverse bacteria and viruses which utilize the raft domain to gain entry into the cell (Pelkmans (2002) Science 296, 535-539). In more detail, SV40 is transported to the endoplasmic reticulum upon caveolae-mediated endocytosis via caveosomes (Pelkmans (2001) Nature Cell Biol. 3, 473-483), as well as by non-caveolar, lipid raft-mediated endocytosis (Damm (2005) J. Cell Biol. 168, 477-488).

The SV40 assay described herein is used as a screen for compounds which may inhibit bacterial or viral infection at the stage of caveolar incorporation, endocytosis and early intracellular trafficking. This mechanism is particularly relevant to infection by respiratory syncytial virus, coronaviruses (e.g. causing SARS or upper respiratory tract infections) and *Mycobacterium* spp. leading to tuberculosis.

In contrast, vesicular stomatitis virus (VSV) enters cells via clathrin-mediated endocytosis into early and late endosomes (Sieczkarski (2003) Traffic 4, 333-343). Thus, the VSV assay described herein serves as a proof-of-concept counterscreen revealing compounds which gain entry into cells via a mechanism independent from caveolae/lipid raft-mediated endocytosis.

Cell Culture

HeLa cells were obtained from DSMZ, Braunschweig, and maintained in D-MEM medium (Gibco BRL) without phenol red supplemented with 10% fetal bovine serum (FBS; PAN Biotech GmbH), 2 mM L-glutamine and 1% penicillin-streptomycin. The cells were incubated at 37° C. in 5% carbon dioxide. The cell number was determined with CASY cell counter (Schärfe System GmbH) and were seeded using the Multidrop 384 dispenser (Thermo). The following cell numbers were seeded per well (in 100 µL medium) in 96-well plates (Greiner) the day before adding the chemical compounds: VSV, immediately, 10000 cells per well; SV40, immediately, 7500 cells per well.

Screens

Three master plates were prepared using dimethylsulfoxide (DMSO), triethyleneglycol monoethyl ether (TEGME) or a mixture of 30% DMSO and 70% TEGME, depending on compound solubility. The concentration of test compound was 3 mM. The substances were transferred into 96-well glass plates (100 µL; 6×9 format) and were diluted 1:100 prior to addition to the cells.

The screens were divided into cytotoxical and a functional part, whereby the toxicity profile (comprising Adenylate-kinase release, live/dead assay and apoptosis assay) were performed first in order to assure non-toxic concentrations of substances. According to the results the substances were diluted with the corresponding solvent. The screen was performed in triplicates and repeated two times with the final concentration of the substances for all assays.

The master plates were stored at −20° C. For the preparation of the working solution the library containing plates were defrosted at 37° C. The substances were diluted in D-MEM medium without serum. The medium was removed from the cells and the working solution was added to each of the triplicate plates. Growth control medium was added and additional specific controls for each assay were applied. Finally, serum was supplied to the cells, and the plates were incubated at 37° C. in an atmosphere containing 5% carbon dioxide.

VSV Infection Assay

VSV-GFP were added immediately after substance addition to the cells in a concentration that gave rise to approximately 50% infected cells. After 4 h incubation the cells were fixed with paraformaldehyde, washed and stained with DRAQ5™. A microscopic analysis with the automated confocal fluorescence microscope OPERA (Evotec Technologies GmbH) was performed, using 488 and 633 nm laser excitation and a water-immersion 20×-objective. In a fully automated manner, 10 images per well were taken, the total number of cells (DRAQ5) and the number of infected cells (VSV-GFP) were determined by automated image analysis and average and standard deviations for triplicates calculated. The VSV infection (in percentage) was calculated by dividing the number of VSV infected nuclei with the total number of nuclei (DRAQ5 stained), multiplied by 100%. The calculated values are expressed as percentage of untreated cells.

SV40 Infection Assay

Wild type SV40 viruses were added immediately after substance addition to the cells. After 36 h incubation the cells were fixed with paraformaldehyde, washed and stained with DRAQ5™. A monoclonal antibody directly conjugated to Alexa Fluor 488 was used to detect T-antigen expression. A microscopic analysis with the automated confocal fluorescence microscope OPERA (Evotec Technologies GmbH) was performed, using 488 and 633 nm laser excitation and a water-immersion 20×-objective. In a fully automated manner, 10 images per well were taken, the total number of cells (DRAQ5) and the number of infected cells (monoclonal antibody bound to SV40 T-antigen) were determined by automated image analysis and average and standard deviations for triplicates calculated. The SV40 infection (in percentage) was calculated by dividing the number of SV40 infected nuclei with the total number of nuclei (DRAQ5 stained), multiplied by 100%. The calculated values are expressed as percentage of untreated cells.

Quantification of Results

The raw data of the SV 40 assay are counts of successfully infected and total cells, determined per well of a 96-well plate. (Total cells are stained by DRAQ5, while the infected cells are counted by specific immuno-histochemical staining of expressed SV-40 T-Antigen as described above). First the ratio of infected to total cells is determined in the following manner.

In each individual assay three wells on three parallel plates per test compound are evaluated, the ratios of infected to total cells are averaged and standard deviation is determined. The data are then transformed to percentages: Controls or solvent controls are set as 100% and data for each test compound are transformed to percentage values with respect to the appropriate solvent control. Each test compound was subjected to two or three independent assays. The average % controls and % standard deviations are determined as averages of % control and % standard deviations of the individual, independent assays. Finally, the inhibition value is calculated using the following formula:

% inhibition=100−% control.

Results: Compound 10a provided a particularly good result in the SV40 infection assay. When tested at a concentration of 6 µM, SV40 infection was inhibited by 37.2% compared to solvent control alone. Thus, compound 10a is particularly preferred for the pharmaceutical intervention in the case of the viral and bacterial infections described above. In contrast, no inhibitory effect on viral infection at all was observed when testing compound 10a in the VSV counterscreen, thus proving the working hypothesis provided herein for the mode of action of the compounds described in this invention.

Example 25

HIV Assay

In order to evaluate their specific usefulness for the development of pharmaceutical compositions used for the treatment of Acquired Immune Deficiency Syndrome (AIDS), which is caused by HIV infection, compounds were tested for inhibition of infection of HeLa TZM cells by HIV-1 strain NL4-3 (laboratory adapted B-type strain). TZM is a CD4-positive HIV-infectable HeLa derivative that contains an HIV-1 LTR-driven luciferase reporter gene. HIV-infection leads to production of the viral trans-activator Tat which induces luciferase expression and luciferase activity can thus be used to score for infected cells.

Test compounds were provided as solutions in dimethylsulfoxide (DMSO), triethyleneglycol monoethyl ether (TEGME) or a mixture of 30% DMSO and 70% TEGME, depending on compound solubility. The concentration of test compound in those stock solutions was 3 mM.

All assays were performed in duplicate. Prior to harvest, cells were analyzed by microscopy for visible cytotoxic effects.

In general, infection with HIV-1 NL4-3 led to ca. 5000-10000 arbitrary light units with some variation depending on the experiment and the use of solvent. PBS controls and solvent controls without any virus yielded 100-200 arbitrary light units.

On the first day, around 50000 TZM cells per well were seeded in 48-well plates. Next day compounds were thawed at 37° C., briefly vortexed and diluted 1:100 in cell culture medium directly before addition to tissue culture cells. 2 μL compound solution was added to 148 μL DMEM (containing 10% FCS and antibiotics) and mixed. The medium was removed from TZM cells and 150 μL of compound-containing medium was added. Subsequently, cells were incubated for 24 h at 37° C. in an atmosphere containing 5% carbon dioxide. 50 μL virus (produced from HIV-1, strain NL4-3 infected MT-4 cells) in RPMI1640 medium (containing 10% FCS and antibiotics) were added and cells were incubated for 24 h at 37° C. in an atmosphere containing 5% carbon dioxide. On the third day, the medium was removed, cells were washed once with DMEM, and 100 μL DMEM were added followed by 100 μL Steady-Glo substrate. Cells were incubated for 30-60 min at room temperature, then 180 μL were transferred from the 48-well plate to a 96-well plate, and luciferase activity was measured using a TECAN plate luminometer (5s per well). Both, solvent controls with and without virus were performed.

Quantification of Results

Each assay plate contains duplicates for each test compound and the appropriate solvent controls. When recording Luminometer readings, a background of uninfected cell controls is subtracted. Duplicates are averaged and converted to % control by dividing the average by the average of the relevant solvent control and multiplying by 100. Assays are repeated once or twice, and final results were determined by averaging the % controls from the two or three independent assays.

Finally, the inhibition value is calculated using the following formula:

% inhibition=100−% control

Results: Four compounds that tested positive in the initial DLRA and thus, identified as disrafters, 10a, 10v, 10w and 10x, were evaluated in the HIV infection assay They provided good results. 10a inhibited HIV infection by 75% at a concentration of 30 μM, while 10v inhibited the same process by 45% at 20 μM concentration compared to solvent. Similarly, compound 10w inhibited infection by 52% (at 20 μM) and compound 10x inhibited HIV infection by 63% (at 30 μM). Thus, these substances are preferred compounds for the pharmaceutical intervention in the case of AIDS.

The invention claimed is:

1. A composition comprising a compound having formula 1 and a pharmaceutically acceptable excipient:

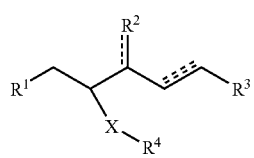

1 wherein
  ≡≡≡ is a single bond, a double bond or a triple bond;
  X is selected from NH, NHCO, NHCONH, NHCO$_2$ and NHSO$_2$;
  $R^1$ is OR, NR$_2$ or OPO$_3^{2-}$ or OCO(C$_{1-4}$ alkyl), wherein R is H or C$_{1-4}$ alkyl;
  $R^2$ is NH$_2$, NH(C$_{1-4}$ alkyl), OH, H, halogen, O, N(C$_{1-4}$ alkyl)$_2$ or O(C$_{1-4}$ alkyl), provided that if $R^2$ is O then ≡≡≡ is a double bond, in all other cases ≡≡≡ is a single bond;
  $R^3$ is a C$_{9-25}$ hydrocarbon group, wherein one or more hydrogens are optionally replaced by halogen;
  $R^4$ is a group of the following formula 2:

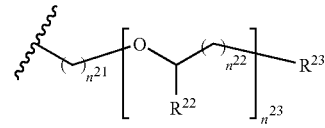

2 wherein
  $n^{21}$ is an integer from 1 to 3, with the proviso that $n^{21}$ is not 1 if X is NH, NHCONH or NHCO$_2$;
  $n^{22}$ is an integer of 1 or 2;
  $n^{23}$ is an integer from 1 to 5;
  each $R^{22}$ is independently H or C$_{1-3}$ alkyl;
  $R^{23}$ is O—$R^{21}$ or NH—$R^{24}$;
  $R^{21}$ is C$_{1-4}$ alkyl, CO(C$_{1-4}$alkyl) or H; and
  $R^{24}$ is C$_{1-4}$ alkyl, CO(C$_{1-4}$alkyl) or H;
  or a pharmaceutically acceptable salt thereof.

2. The composition of claim 1, wherein X is NHCO.

3. The composition of claim 1, wherein $R^1$ is OH or OPO$_3^{2-}$.

4. The composition of claim 1, wherein $R^2$ is OH or OCH$_3$.

5. The composition of claim 1, wherein $R^3$ is a C$_{13-15}$ alkyl group.

6. The composition of claim 1, wherein the compound having formula 1 is a compound having one of the following formulae 10g or 10h:

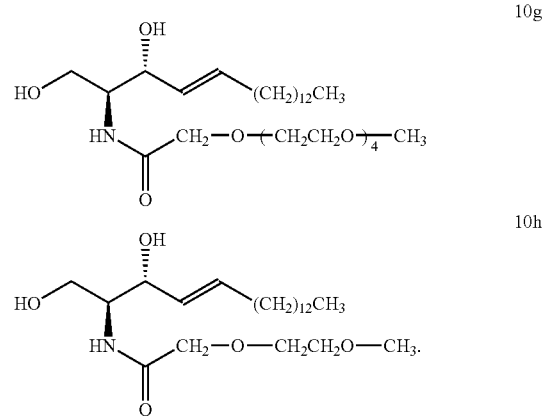

10g

10h

7. The composition of claim 1, wherein the compound having formula 1 is a compound having one of the following formulae 10v, 10w or 10x:

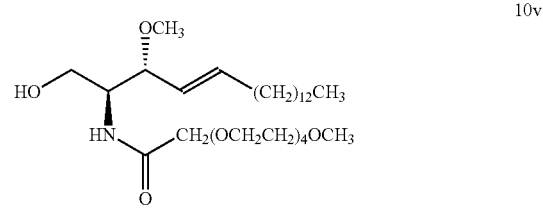

10v

-continued
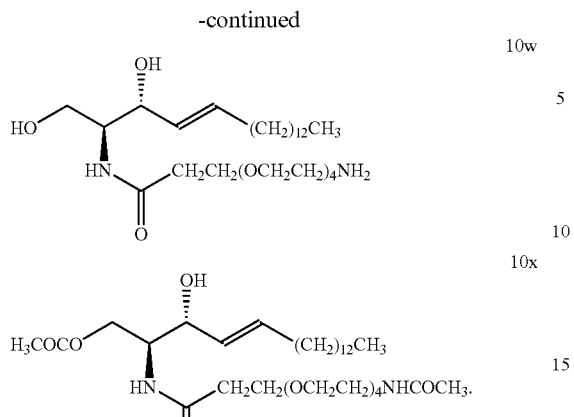
8. The composition of claim 1, wherein said compound having formula 1 is a compound having one of the following formulae 10g, 10h, 10v, 10w or 10x:
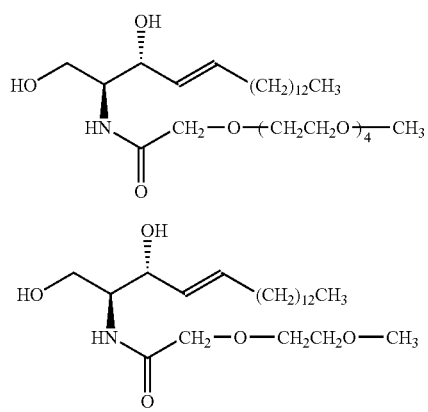
-continued
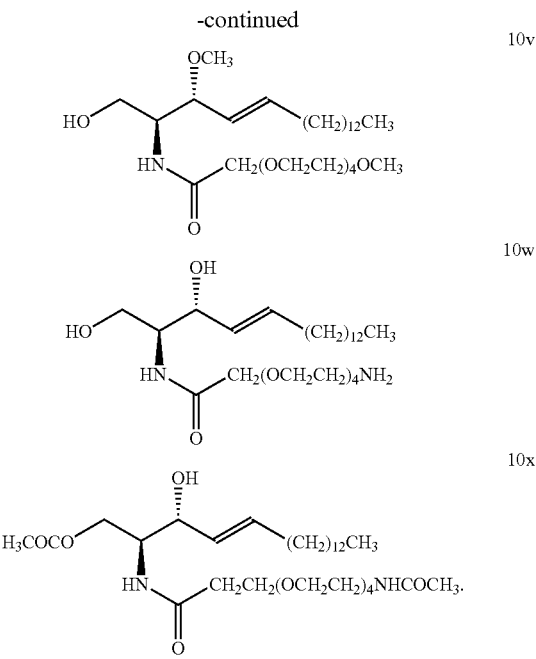
9. The composition of claim 8, wherein said compound has the formula 10w:
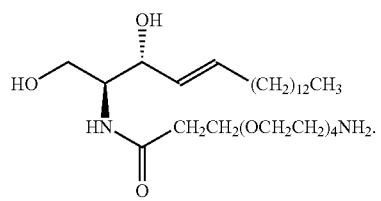
* * * * *

UNITED STATES PATENT AND TRADEMARK OFFICE
CERTIFICATE OF CORRECTION

PATENT NO. : 7,629,385 B2  
APPLICATION NO. : 11/571354  
DATED : December 8, 2009  
INVENTOR(S) : Tobias Braxmeier et al.

It is certified that error appears in the above-identified patent and that said Letters Patent is hereby corrected as shown below:

In claim 8, column 50, lines 12-18, delete chemical drawing labeled 10w and insert the following:

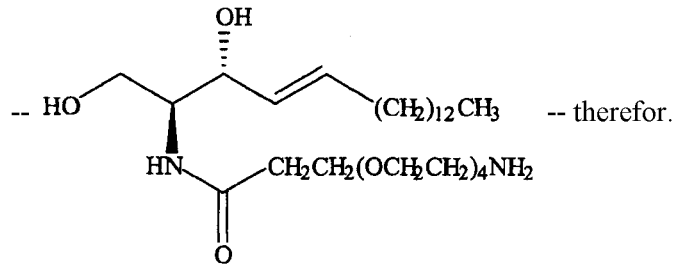 -- therefor.

Signed and Sealed this

Sixteenth Day of March, 2010

David J. Kappos  
*Director of the United States Patent and Trademark Office*